(12) United States Patent
Hart

(10) Patent No.: US 10,198,965 B2
(45) Date of Patent: Feb. 5, 2019

(54) SIMULATED STAPLING AND ENERGY BASED LIGATION FOR SURGICAL TRAINING

(71) Applicant: Applied Medical Resources Corporation, Rancho Santa Margarita, CA (US)

(72) Inventor: Charles C. Hart, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 134 days.

(21) Appl. No.: 13/957,973

(22) Filed: Aug. 2, 2013

(65) Prior Publication Data

US 2014/0038151 A1 Feb. 6, 2014

Related U.S. Application Data

(60) Provisional application No. 61/679,494, filed on Aug. 3, 2012.

(51) Int. Cl.
*G09B 23/28* (2006.01)
*A61B 17/32* (2006.01)
(Continued)

(52) U.S. Cl.
CPC ........... *G09B 23/28* (2013.01); *G09B 23/285* (2013.01); *A61B 17/068* (2013.01);
(Continued)

(58) Field of Classification Search
CPC .......... A61B 17/07207; A61B 18/1445; A61B 17/068; A61B 2017/2936;
(Continued)

(56) References Cited

U.S. PATENT DOCUMENTS

| 184,573 A | 11/1876 | Becker |
|---|---|---|
| 2,127,774 A | 8/1938 | Jacobson |

(Continued)

FOREIGN PATENT DOCUMENTS

| CN | 2421706 Y | 2/2001 |
|---|---|---|
| CN | 2751372 Y | 1/2006 |

(Continued)

OTHER PUBLICATIONS

European Patent Office, The International Search Report and Written Opinion for International Application No. PCT/US2012/070971, dated Jul. 4, 2014, entitled "Advanced Surgical Simulation Constructions and Methods".

(Continued)

*Primary Examiner* — Jack Yip
(74) *Attorney, Agent, or Firm* — John F. Heal; Rimas T. Lukas

(57) ABSTRACT

An inexpensive and practical surgical training system to train practitioners in the use of surgical stapling and energy-based ligation instruments and procedures is provided. The system comprises a modified or simulated surgical instrument such as linear surgical stapling device having a fixed anvil and an opposed, movable jaw sized and configured to be closed upon a simulated tissue structure. A marking or inking element is associated with the jaw and anvil of the stapling device and configured to impose a visible pattern on the surfaces of simulated tissue placed between the anvil and jaw. A pressure sensitive adhesive or other adhesive is associated with the inner surfaces of the simulated tissue that is activated upon compression between the anvil and jaw to simulate surgical occlusion.

9 Claims, 12 Drawing Sheets

(51) Int. Cl.
  *A61B 17/072* (2006.01)
  *A61B 18/14* (2006.01)
  *A61B 17/068* (2006.01)
  *A61B 17/29* (2006.01)

(52) U.S. Cl.
  CPC . *A61B 17/07207* (2013.01); *A61B 17/320092* (2013.01); *A61B 18/1445* (2013.01); *A61B 2017/2936* (2013.01)

(58) Field of Classification Search
  CPC ........ A61B 17/320092; G06F 19/3437; G09B 23/28; G09B 23/285
  USPC ...................................................... 434/262
  See application file for complete search history.

(56) References Cited

U.S. PATENT DOCUMENTS

| | | |
|---|---|---|
| 2,284,888 A | 6/1942 | Arnell, Jr. |
| 2,324,702 A | 7/1943 | Hoffman et al. |
| 2,345,489 A | 3/1944 | Lord |
| 2,495,568 A | 1/1950 | Coel |
| 3,766,666 A | 10/1973 | Stroop |
| 3,775,865 A | 12/1973 | Rowan |
| 3,789,518 A | 2/1974 | Chase |
| 3,921,311 A | 11/1975 | Beasley et al. |
| 3,991,490 A | 11/1976 | Markman |
| 4,001,951 A | 1/1977 | Fasse |
| 4,001,952 A | 1/1977 | Kleppinger |
| 4,321,047 A | 3/1982 | Landis |
| 4,323,350 A | 4/1982 | Bowden, Jr. |
| 4,332,569 A | 6/1982 | Burbank |
| 4,371,345 A | 2/1983 | Palmer et al. |
| 4,386,917 A | 6/1983 | Forrest |
| 4,459,113 A | 7/1984 | Boscaro Gatti et al. |
| 4,481,001 A * | 11/1984 | Graham et al. ............... 434/267 |
| 4,596,528 A | 6/1986 | Lewis et al. |
| 4,726,772 A | 2/1988 | Amplatz |
| 4,737,109 A | 4/1988 | Abramson |
| 4,789,340 A | 12/1988 | Zikria |
| 4,832,978 A | 5/1989 | Lesser |
| 4,867,686 A | 9/1989 | Goldstein |
| 4,907,973 A | 3/1990 | Hon |
| 4,938,696 A | 7/1990 | Foster et al. |
| 4,940,412 A | 7/1990 | Blumenthal |
| 5,061,187 A | 10/1991 | Jerath |
| 5,083,962 A | 1/1992 | Pracas |
| 5,104,328 A | 4/1992 | Lounsbury |
| 5,149,270 A | 9/1992 | McKeown |
| 5,180,308 A | 1/1993 | Garito et al. |
| 5,230,630 A | 7/1993 | Burgett |
| 5,273,435 A | 12/1993 | Jacobson |
| 5,295,694 A | 3/1994 | Levin |
| 5,310,348 A | 5/1994 | Miller |
| 5,318,448 A | 6/1994 | Garito et al. |
| 5,320,537 A | 6/1994 | Watson |
| 5,358,408 A | 10/1994 | Medina |
| 5,368,487 A | 11/1994 | Medina |
| 5,380,207 A | 1/1995 | Siepser |
| 5,403,191 A | 4/1995 | Tuason |
| 5,425,644 A | 6/1995 | Szinicz |
| 5,425,731 A | 6/1995 | Daniel et al. |
| 5,472,345 A | 12/1995 | Eggert |
| 5,518,406 A | 5/1996 | Waters |
| 5,518,407 A | 5/1996 | Greenfield et al. |
| 5,520,633 A | 5/1996 | Costin |
| 5,541,304 A | 7/1996 | Thompson |
| 5,620,326 A | 4/1997 | Younker |
| 5,720,742 A | 2/1998 | Zacharias |
| 5,722,836 A | 3/1998 | Younker |
| 5,727,948 A | 3/1998 | Jordan |
| 5,743,730 A | 4/1998 | Clester et al. |
| 5,762,458 A | 6/1998 | Wang et al. |
| 5,769,640 A | 6/1998 | Jacobus et al. |
| 5,775,916 A | 7/1998 | Cooper et al. |
| 5,785,531 A | 7/1998 | Leung |
| 5,800,178 A | 9/1998 | Gillio |
| 5,803,746 A | 9/1998 | Barrie et al. |
| 5,807,378 A | 9/1998 | Jensen et al. |
| 5,810,880 A | 9/1998 | Jensen et al. |
| 5,814,038 A | 9/1998 | Jensen et al. |
| 5,850,033 A | 12/1998 | Mirzeabasov et al. |
| 5,855,583 A | 1/1999 | Wang et al. |
| 5,873,732 A | 2/1999 | Hasson |
| 5,873,863 A | 2/1999 | Komlosi |
| 5,908,302 A | 6/1999 | Goldfarb |
| 5,947,743 A | 9/1999 | Hasson |
| 5,951,301 A | 9/1999 | Younker |
| 6,080,181 A | 6/2000 | Jensen et al. |
| 6,083,008 A | 7/2000 | Yamada et al. |
| 6,113,395 A | 9/2000 | Hon |
| 6,234,804 B1 | 5/2001 | Yong |
| 6,336,812 B1 | 1/2002 | Cooper et al. |
| 6,398,557 B1 | 6/2002 | Hoballah |
| 6,413,264 B1 | 7/2002 | Jensen et al. |
| 6,474,993 B1 | 11/2002 | Grund et al. |
| 6,485,308 B1 | 11/2002 | Goldstein |
| 6,488,507 B1 | 12/2002 | Stoloff et al. |
| 6,497,902 B1 | 12/2002 | Ma |
| 6,511,325 B1 | 1/2003 | Lalka et al. |
| 6,517,354 B1 | 2/2003 | Levy |
| 6,568,941 B1 | 5/2003 | Goldstein |
| 6,620,174 B2 | 9/2003 | Jensen et al. |
| 6,654,000 B2 | 11/2003 | Rosenberg |
| 6,659,776 B1 | 12/2003 | Aumann et al. |
| 6,773,263 B2 | 8/2004 | Nicholls et al. |
| 6,780,016 B1 | 8/2004 | Toly |
| 6,817,973 B2 | 11/2004 | Merril et al. |
| 6,820,025 B2 | 11/2004 | Bachmann et al. |
| 6,854,976 B1 | 2/2005 | Suhr |
| 6,857,878 B1 | 2/2005 | Chosack et al. |
| 6,863,536 B1 | 3/2005 | Fisher et al. |
| 6,866,514 B2 | 3/2005 | Von Roeschlaub et al. |
| 6,887,082 B2 | 5/2005 | Shun |
| 6,929,481 B1 | 8/2005 | Alexander et al. |
| 6,939,138 B2 | 9/2005 | Chosack et al. |
| 6,950,025 B1 | 9/2005 | Nguyen |
| 6,960,617 B2 | 11/2005 | Omidian et al. |
| 6,997,719 B2 | 2/2006 | Wellman et al. |
| 7,008,232 B2 | 3/2006 | Brassel |
| 7,018,327 B1 | 3/2006 | Conti |
| 7,025,064 B2 | 4/2006 | Wang et al. |
| 7,056,123 B2 | 6/2006 | Gregorio et al. |
| 7,080,984 B1 | 7/2006 | Cohen |
| 7,118,582 B1 | 10/2006 | Wang et al. |
| 7,255,565 B2 | 8/2007 | Keegan |
| 7,269,532 B2 | 9/2007 | David et al. |
| 7,272,766 B2 | 9/2007 | Sakezles |
| 7,300,450 B2 | 11/2007 | Vleugels et al. |
| 7,364,582 B2 | 4/2008 | Lee |
| 7,404,716 B2 | 7/2008 | Gregorio et al. |
| 7,419,376 B2 | 9/2008 | Sarvazyan et al. |
| 7,427,199 B2 | 9/2008 | Sakezles |
| 7,431,189 B2 | 10/2008 | Shelton, IV et al. |
| 7,441,684 B2 | 10/2008 | Shelton, IV et al. |
| 7,465,168 B2 | 12/2008 | Allen et al. |
| 7,467,075 B2 | 12/2008 | Humphries et al. |
| 7,544,062 B1 | 6/2009 | Hauschild et al. |
| 7,549,866 B2 | 6/2009 | Cohen et al. |
| 7,553,159 B1 | 6/2009 | Arnal et al. |
| 7,575,434 B2 | 8/2009 | Palakodeti |
| 7,594,815 B2 | 9/2009 | Toly |
| 7,621,749 B2 | 11/2009 | Munday |
| 7,646,901 B2 | 1/2010 | Murphy et al. |
| 7,648,367 B1 | 1/2010 | Makower et al. |
| 7,648,513 B2 | 1/2010 | Green et al. |
| 7,651,332 B2 | 1/2010 | Dupuis et al. |
| 7,677,897 B2 | 3/2010 | Sakezles |
| 7,775,916 B1 | 8/2010 | Mahoney |
| 7,780,451 B2 | 8/2010 | Willobee et al. |
| 7,802,990 B2 | 9/2010 | Korndorffer et al. |
| 7,803,151 B2 | 9/2010 | Whitman |
| 7,806,696 B2 | 10/2010 | Alexander et al. |
| 7,819,799 B2 | 10/2010 | Merril et al. |

(56) References Cited

U.S. PATENT DOCUMENTS

| | | |
|---|---|---|
| 7,833,018 B2 | 11/2010 | Alexander et al. |
| 7,837,473 B2 | 11/2010 | Koh |
| 7,850,454 B2 | 12/2010 | Toly |
| 7,850,456 B2 | 12/2010 | Chosack et al. |
| 7,854,612 B2 | 12/2010 | Frassica et al. |
| 7,857,626 B2 | 12/2010 | Toly |
| 7,866,983 B2 | 1/2011 | Hemphill et al. |
| 7,931,470 B2 | 4/2011 | Alexander et al. |
| 7,931,471 B2 | 4/2011 | Senagore et al. |
| 7,988,992 B2 | 8/2011 | Omidian et al. |
| 7,993,140 B2 | 8/2011 | Sakezles |
| 7,997,903 B2 | 8/2011 | Hasson et al. |
| 8,007,281 B2 | 8/2011 | Toly |
| 8,007,282 B2 | 8/2011 | Gregorio et al. |
| 8,016,818 B2 | 9/2011 | Ellis et al. |
| 8,021,162 B2 | 9/2011 | Sui |
| 8,048,088 B2 | 11/2011 | Green et al. |
| 8,083,691 B2 | 12/2011 | Goldenberg et al. |
| 8,116,847 B2 | 2/2012 | Gattani et al. |
| 8,137,110 B2 | 3/2012 | Sakezles |
| 8,157,145 B2 | 4/2012 | Shelton, IV et al. |
| 8,197,464 B2 | 6/2012 | Krever et al. |
| 8,205,779 B2 | 6/2012 | Ma et al. |
| 8,221,129 B2 | 7/2012 | Parry et al. |
| 8,297,982 B2 | 10/2012 | Park et al. |
| 8,308,817 B2 | 11/2012 | Egilsson et al. |
| 8,323,028 B2 | 12/2012 | Matanhelia |
| 8,323,029 B2 | 12/2012 | Toly |
| 8,328,560 B2 | 12/2012 | Niblock et al. |
| 8,342,851 B1 | 1/2013 | Speeg et al. |
| 8,403,674 B2 | 3/2013 | Feygin et al. |
| 8,403,675 B2 | 3/2013 | Stoianovici et al. |
| 8,403,676 B2 | 3/2013 | Frassica et al. |
| 8,408,920 B2 | 4/2013 | Speller |
| 8,425,234 B2 | 4/2013 | Sakezles |
| 8,439,687 B1 | 5/2013 | Morriss et al. |
| 8,442,621 B2 | 5/2013 | Gorek et al. |
| 8,454,368 B2 | 6/2013 | Ault et al. |
| 8,459,094 B2 | 6/2013 | Yanni |
| 8,459,520 B2 | 6/2013 | Giordano et al. |
| 8,460,002 B2 | 6/2013 | Wang et al. |
| 8,469,715 B2 | 6/2013 | Ambrozio |
| 8,469,716 B2 | 6/2013 | Fedotov et al. |
| 8,480,407 B2 | 7/2013 | Campbell et al. |
| 8,480,408 B2 | 7/2013 | Ishii et al. |
| 8,491,309 B2 | 7/2013 | Parry et al. |
| 8,500,753 B2 | 8/2013 | Green et al. |
| 8,512,044 B2 | 8/2013 | Sakezles |
| 8,517,243 B2 | 8/2013 | Giordano et al. |
| 8,521,252 B2 | 8/2013 | Diez |
| 8,535,062 B2 | 9/2013 | Nguyen |
| 8,544,711 B2 | 10/2013 | Ma et al. |
| 8,556,635 B2 | 10/2013 | Toly |
| 8,608,483 B2 | 12/2013 | Trotta et al. |
| 8,613,621 B2 | 12/2013 | Henderickson et al. |
| 8,636,520 B2 | 1/2014 | Iwasaki et al. |
| D699,297 S | 2/2014 | Bahsooun et al. |
| 8,641,423 B2 | 2/2014 | Gumkowski |
| 8,647,125 B2 | 2/2014 | Johns et al. |
| 8,678,831 B2 | 3/2014 | Trotta et al. |
| 8,679,279 B2 | 3/2014 | Thompson et al. |
| 8,696,363 B2 | 4/2014 | Gray et al. |
| 8,708,213 B2 | 4/2014 | Shelton, IV et al. |
| 8,708,707 B2 | 4/2014 | Hendrickson et al. |
| 8,764,449 B2 | 7/2014 | Rios et al. |
| 8,764,452 B2 | 7/2014 | Pravong et al. |
| 8,800,839 B2 | 8/2014 | Beetel |
| 8,801,437 B2 | 8/2014 | Mousques |
| 8,801,438 B2 | 8/2014 | Sakezles |
| 8,807,414 B2 | 8/2014 | Ross et al. |
| 8,808,004 B2 | 8/2014 | Misawa et al. |
| 8,808,311 B2 | 8/2014 | Heinrich et al. |
| 8,814,573 B2 | 8/2014 | Nguyen |
| 8,827,988 B2 | 9/2014 | Belson et al. |
| 8,840,628 B2 | 9/2014 | Green et al. |
| 8,870,576 B2 | 10/2014 | Millon et al. |
| 8,888,498 B2 | 11/2014 | Bisaillon et al. |
| 8,893,946 B2 | 11/2014 | Boudreaux et al. |
| 8,911,238 B2 | 12/2014 | Forsythe |
| 8,915,742 B2 | 12/2014 | Hendrickson et al. |
| 8,945,095 B2 | 2/2015 | Blumenkranz et al. |
| 8,961,190 B2 | 2/2015 | Hart et al. |
| 8,966,954 B2 | 3/2015 | Ni et al. |
| 8,968,003 B2 | 3/2015 | Hendrickson et al. |
| 9,008,989 B2 | 4/2015 | Wilson et al. |
| 9,017,080 B1 | 4/2015 | Placik |
| 9,026,247 B2 | 5/2015 | White |
| 9,050,201 B2 | 6/2015 | Egilsson et al. |
| 9,056,126 B2 | 6/2015 | Hersel et al. |
| 9,070,306 B2 | 6/2015 | Rappel et al. |
| 9,087,458 B2 | 7/2015 | Shim et al. |
| 9,117,377 B2 | 8/2015 | Shim et al. |
| 9,119,572 B2 | 9/2015 | Gorek et al. |
| 9,123,261 B2 | 9/2015 | Lowe |
| 9,129,054 B2 | 9/2015 | Nawana et al. |
| 9,196,176 B2 | 11/2015 | Hager et al. |
| 9,226,799 B2 | 1/2016 | Lightcap et al. |
| 9,257,055 B2 | 2/2016 | Endo et al. |
| 9,265,587 B2 | 2/2016 | Vancamberg et al. |
| 9,295,468 B2 | 3/2016 | Heinrich et al. |
| 9,351,714 B2 | 5/2016 | Ross et al. |
| 9,336,694 B2 | 6/2016 | Shim et al. |
| 9,358,682 B2 | 6/2016 | Ruiz Morales |
| 9,364,224 B2 | 6/2016 | Nicholas et al. |
| 9,364,279 B2 | 6/2016 | Houser et al. |
| 9,370,361 B2 | 6/2016 | Viola et al. |
| 9,373,270 B2 | 6/2016 | Miyazaki |
| 9,439,649 B2 | 9/2016 | Shelton, IV et al. |
| 9,439,733 B2 | 9/2016 | Ha et al. |
| 9,449,532 B2 | 9/2016 | Black et al. |
| 9,468,438 B2 | 10/2016 | Baber et al. |
| 2001/0019818 A1 | 9/2001 | Yong |
| 2002/0165541 A1* | 11/2002 | Whitman ........ A61B 17/320068 606/48 |
| 2002/0168619 A1 | 11/2002 | Provenza |
| 2003/0031993 A1 | 2/2003 | Pugh |
| 2003/0091967 A1 | 5/2003 | Chosack et al. |
| 2003/0176770 A1 | 9/2003 | Merril et al. |
| 2004/0005423 A1 | 1/2004 | Dalton et al. |
| 2004/0248072 A1 | 12/2004 | Gray et al. |
| 2005/0008997 A1 | 1/2005 | Herman |
| 2005/0026125 A1 | 2/2005 | Toly |
| 2005/0084833 A1 | 4/2005 | Lacey et al. |
| 2005/0131390 A1 | 6/2005 | Heinrich et al. |
| 2005/0142525 A1 | 6/2005 | Cotin et al. |
| 2005/0192595 A1 | 9/2005 | Green et al. |
| 2005/0196739 A1 | 9/2005 | Moriyama |
| 2005/0196740 A1 | 9/2005 | Moriyana |
| 2005/0214727 A1 | 9/2005 | Stoianovici et al. |
| 2006/0046235 A1 | 2/2006 | Alexander et al. |
| 2006/0252019 A1 | 11/2006 | Burkitt et al. |
| 2006/0275741 A1 | 12/2006 | Chewning et al. |
| 2007/0074584 A1 | 4/2007 | Talarico et al. |
| 2007/0077544 A1 | 4/2007 | Lemperle et al. |
| 2007/0078484 A1 | 4/2007 | Talarico et al. |
| 2007/0148626 A1 | 6/2007 | Ikeda |
| 2007/0166682 A1 | 7/2007 | Yarin et al. |
| 2007/0179528 A1* | 8/2007 | Soltz ................ A61B 17/072 606/219 |
| 2007/0197895 A1 | 8/2007 | Nycz et al. |
| 2007/0225734 A1 | 9/2007 | Bell et al. |
| 2007/0275359 A1 | 11/2007 | Rotnes et al. |
| 2008/0032272 A1 | 2/2008 | Palakodeti |
| 2008/0032273 A1 | 2/2008 | Macnamara et al. |
| 2008/0052034 A1 | 2/2008 | David et al. |
| 2008/0064017 A1 | 3/2008 | Grundmeyer, III |
| 2008/0076101 A1 | 3/2008 | Hyde et al. |
| 2008/0097501 A1 | 4/2008 | Blier |
| 2008/0108869 A1 | 5/2008 | Sanders et al. |
| 2008/0114381 A1* | 5/2008 | Voegele ............ A61B 17/10 606/151 |
| 2008/0187895 A1 | 8/2008 | Sakezles |
| 2008/0188948 A1 | 8/2008 | Flatt |
| 2008/0299529 A1 | 12/2008 | Schaller |

(56) References Cited

U.S. PATENT DOCUMENTS

| | | |
|---|---|---|
| 2009/0246747 A1 | 1/2009 | Buckman, Jr. |
| 2009/0068627 A1 | 3/2009 | Toly |
| 2009/0092651 A1* | 4/2009 | Shah ............... A61L 27/34 424/422 |
| 2009/0142739 A1 | 6/2009 | Wang et al. |
| 2009/0142741 A1 | 6/2009 | Ault et al. |
| 2009/0143642 A1 | 6/2009 | Takahashi et al. |
| 2009/0176196 A1 | 7/2009 | Niblock et al. |
| 2009/0187079 A1 | 7/2009 | Albrecht et al. |
| 2009/0298034 A1 | 12/2009 | Parry et al. |
| 2010/0047752 A1 | 2/2010 | Chan et al. |
| 2010/0094312 A1 | 4/2010 | Ruiz Morales et al. |
| 2010/0099067 A1 | 4/2010 | Agro |
| 2010/0167248 A1 | 7/2010 | Ryan |
| 2010/0167249 A1 | 7/2010 | Ryan |
| 2010/0167250 A1 | 7/2010 | Ryan et al. |
| 2010/0167253 A1 | 7/2010 | Ryan et al. |
| 2010/0167254 A1 | 7/2010 | Nguyen |
| 2010/0196867 A1 | 8/2010 | Geerligs et al. |
| 2010/0204713 A1 | 8/2010 | Ruiz Morales |
| 2010/0209899 A1 | 8/2010 | Park |
| 2010/0258611 A1 | 10/2010 | Smith et al. |
| 2010/0273136 A1 | 10/2010 | Kandasami et al. |
| 2010/0279263 A1 | 11/2010 | Duryea |
| 2010/0324541 A1 | 12/2010 | Whitman |
| 2011/0014596 A1* | 1/2011 | Kurenov et al. ............... 434/262 |
| 2011/0046637 A1 | 2/2011 | Patel et al. |
| 2011/0046659 A1 | 2/2011 | Ramstein et al. |
| 2011/0087238 A1 | 4/2011 | Wang et al. |
| 2011/0091855 A1 | 4/2011 | Miyazaki |
| 2011/0137337 A1 | 6/2011 | van den Dool et al. |
| 2011/0200976 A1 | 8/2011 | Hou et al. |
| 2011/0207104 A1 | 8/2011 | Trotta |
| 2011/0218550 A1 | 9/2011 | Ma |
| 2011/0244436 A1 | 10/2011 | Campo |
| 2011/0269109 A2 | 11/2011 | Miyazaki |
| 2011/0281251 A1 | 11/2011 | Mousques |
| 2011/0301620 A1 | 12/2011 | Di Betta et al. |
| 2012/0015337 A1 | 1/2012 | Hendrickson et al. |
| 2012/0015339 A1 | 1/2012 | Hendrickson et al. |
| 2012/0016362 A1 | 1/2012 | Heinrich et al. |
| 2012/0028231 A1 | 2/2012 | Misawa et al. |
| 2012/0045743 A1 | 2/2012 | Misawa et al. |
| 2012/0065632 A1 | 3/2012 | Shadduck |
| 2012/0082970 A1 | 4/2012 | Pravong et al. |
| 2012/0100217 A1 | 4/2012 | Green et al. |
| 2012/0115117 A1 | 5/2012 | Marshall |
| 2012/0115118 A1 | 5/2012 | Marshall |
| 2012/0116391 A1 | 5/2012 | Houser et al. |
| 2012/0148994 A1 | 6/2012 | Hori et al. |
| 2012/0164616 A1 | 6/2012 | Endo et al. |
| 2012/0165866 A1 | 6/2012 | Kaiser et al. |
| 2012/0172873 A1 | 7/2012 | Artale et al. |
| 2012/0179072 A1 | 7/2012 | Kegreiss |
| 2012/0202180 A1 | 8/2012 | Stock et al. |
| 2012/0234895 A1* | 9/2012 | O'Connor et al. ........ 227/176.1 |
| 2012/0264096 A1 | 10/2012 | Taylor et al. |
| 2012/0264097 A1 | 10/2012 | Newcott et al. |
| 2012/0282583 A1 | 11/2012 | Thaler et al. |
| 2012/0282584 A1 | 11/2012 | Millon et al. |
| 2012/0283707 A1 | 11/2012 | Giordano et al. |
| 2012/0288839 A1 | 11/2012 | Crabtree |
| 2012/0308977 A1 | 12/2012 | Tortola |
| 2013/0087597 A1 | 4/2013 | Shelton, IV et al. |
| 2013/0101973 A1 | 4/2013 | Hoke et al. |
| 2013/0105552 A1 | 5/2013 | Weir et al. |
| 2013/0116668 A1 | 5/2013 | Shelton, IV et al. |
| 2013/0157240 A1 | 6/2013 | Hart et al. |
| 2013/0171288 A1 | 7/2013 | Harders |
| 2013/0177890 A1 | 7/2013 | Sakezles |
| 2013/0192741 A1 | 8/2013 | Trotta et al. |
| 2013/0218166 A1 | 8/2013 | Elmore |
| 2013/0224709 A1 | 8/2013 | Riojas et al. |
| 2013/0245681 A1 | 9/2013 | Straehnz et al. |
| 2013/0253480 A1 | 9/2013 | Kimball et al. |
| 2013/0267876 A1 | 10/2013 | Leckenby et al. |
| 2013/0282038 A1 | 10/2013 | Dannaher et al. |
| 2013/0288216 A1 | 10/2013 | Parry, Jr. et al. |
| 2013/0302771 A1 | 11/2013 | Alderete |
| 2013/0324991 A1 | 12/2013 | Clem et al. |
| 2013/0324999 A1 | 12/2013 | Price et al. |
| 2014/0011172 A1 | 1/2014 | Lowe |
| 2014/0017651 A1 | 1/2014 | Sugimoto et al. |
| 2014/0030682 A1 | 1/2014 | Thilenius |
| 2014/0038151 A1 | 2/2014 | Hart |
| 2014/0051049 A1 | 2/2014 | Jarc et al. |
| 2014/0072941 A1 | 3/2014 | Hendrickson et al. |
| 2014/0087345 A1 | 3/2014 | Breslin et al. |
| 2014/0087346 A1 | 3/2014 | Breslin et al. |
| 2014/0087347 A1 | 3/2014 | Tracy et al. |
| 2014/0087348 A1 | 3/2014 | Tracy et al. |
| 2014/0088413 A1 | 3/2014 | Von Bucsh et al. |
| 2014/0093852 A1 | 4/2014 | Poulsen et al. |
| 2014/0093854 A1 | 4/2014 | Poulsen et al. |
| 2014/0099858 A1 | 4/2014 | Hernandez |
| 2014/0106328 A1 | 4/2014 | Loor |
| 2014/0107471 A1 | 4/2014 | Haider et al. |
| 2014/0156002 A1 | 6/2014 | Thompson et al. |
| 2014/0162016 A1 | 6/2014 | Matsui et al. |
| 2014/0170623 A1 | 6/2014 | Jarstad et al. |
| 2014/0186809 A1 | 7/2014 | Hendrickson et al. |
| 2014/0200561 A1 | 7/2014 | Ingmanson et al. |
| 2014/0212861 A1 | 7/2014 | Romano |
| 2014/0220527 A1 | 8/2014 | Li et al. |
| 2014/0220530 A1 | 8/2014 | Merkle et al. |
| 2014/0220532 A1 | 8/2014 | Ghez et al. |
| 2014/0242564 A1 | 8/2014 | Pravong et al. |
| 2014/0246479 A1 | 9/2014 | Baber et al. |
| 2014/0248596 A1 | 9/2014 | Hart et al. |
| 2014/0263538 A1 | 9/2014 | Leimbach et al. |
| 2014/0272878 A1 | 9/2014 | Shim et al. |
| 2014/0272879 A1 | 9/2014 | Shim et al. |
| 2014/0275795 A1 | 9/2014 | Little et al. |
| 2014/0275981 A1 | 9/2014 | Selover et al. |
| 2014/0277017 A1 | 9/2014 | Leimbach et al. |
| 2014/0303643 A1 | 10/2014 | Ha et al. |
| 2014/0303646 A1 | 10/2014 | Morgan et al. |
| 2014/0303660 A1 | 10/2014 | Boyden et al. |
| 2014/0308643 A1 | 10/2014 | Trotta et al. |
| 2014/0342334 A1 | 11/2014 | Black et al. |
| 2014/0349266 A1 | 11/2014 | Choi |
| 2014/0350530 A1 | 11/2014 | Ross et al. |
| 2014/0357977 A1 | 12/2014 | Zhou |
| 2014/0370477 A1 | 12/2014 | Black et al. |
| 2014/0371761 A1 | 12/2014 | Juanpera |
| 2014/0378995 A1 | 12/2014 | Kumar et al. |
| 2015/0031008 A1 | 1/2015 | Black et al. |
| 2015/0037773 A1 | 2/2015 | Quirarte Catano |
| 2015/0038613 A1 | 2/2015 | Sun et al. |
| 2015/0076207 A1 | 3/2015 | Boudreaux et al. |
| 2015/0086955 A1 | 3/2015 | Poniatowski et al. |
| 2015/0132732 A1 | 5/2015 | Hart et al. |
| 2015/0132733 A1 | 5/2015 | Garvik et al. |
| 2015/0135832 A1 | 5/2015 | Blumenkranz et al. |
| 2015/0148660 A1 | 5/2015 | Weiss et al. |
| 2015/0164598 A1 | 6/2015 | Blumenkranz et al. |
| 2015/0187229 A1 | 7/2015 | Wachli et al. |
| 2015/0194075 A1 | 7/2015 | Rappel et al. |
| 2015/0202299 A1 | 7/2015 | Burdick et al. |
| 2015/0209035 A1 | 7/2015 | Zemlock |
| 2015/0209059 A1 | 7/2015 | Trees et al. |
| 2015/0209573 A1 | 7/2015 | Hibner et al. |
| 2015/0228206 A1 | 8/2015 | Shim et al. |
| 2015/0262511 A1 | 9/2015 | Lin et al. |
| 2015/0265431 A1 | 9/2015 | Egilsson et al. |
| 2015/0272571 A1 | 10/2015 | Leimbach et al. |
| 2015/0272574 A1 | 10/2015 | Leimbach et al. |
| 2015/0272580 A1 | 10/2015 | Leimbach et al. |
| 2015/0272581 A1 | 10/2015 | Leimbach et al. |
| 2015/0272583 A1 | 10/2015 | Leimbach et al. |
| 2015/0272604 A1 | 10/2015 | Chowaniec et al. |
| 2015/0332609 A1 | 11/2015 | Alexander |
| 2015/0358426 A1 | 12/2015 | Kimball et al. |
| 2015/0371560 A1 | 12/2015 | Lowe |

(56) References Cited

U.S. PATENT DOCUMENTS

| | | |
|---|---|---|
| 2015/0374378 A1 | 12/2015 | Giordano et al. |
| 2015/0374449 A1 | 12/2015 | Chowaniec et al. |
| 2016/0000437 A1 | 1/2016 | Giordano et al. |
| 2016/0022374 A1 | 1/2016 | Haider et al. |
| 2016/0030240 A1 | 2/2016 | Gonenc et al. |
| 2016/0031091 A1 | 2/2016 | Popovic et al. |
| 2016/0066909 A1 | 3/2016 | Baber et al. |
| 2016/0070436 A1 | 3/2016 | Thomas et al. |
| 2016/0073928 A1 | 3/2016 | Soper et al. |
| 2016/0074103 A1 | 3/2016 | Sartor |
| 2016/0098933 A1 | 4/2016 | Reiley et al. |
| 2016/0104394 A1 | 4/2016 | Miyazaki |
| 2016/0117956 A1 | 4/2016 | Larsson et al. |
| 2016/0133158 A1 | 5/2016 | Sui et al. |
| 2016/0140876 A1 | 5/2016 | Jabbour et al. |
| 2016/0199059 A1 | 7/2016 | Shelton, IV et al. |
| 2016/0220150 A1 | 8/2016 | Sharonov |
| 2016/0220314 A1 | 8/2016 | Huelman et al. |
| 2016/0225288 A1 | 8/2016 | East et al. |
| 2016/0232819 A1 | 8/2016 | Hofstetter et al. |
| 2016/0235494 A1 | 8/2016 | Shelton, IV et al. |
| 2016/0256187 A1 | 9/2016 | Shelton, IV et al. |
| 2016/0256229 A1 | 9/2016 | Morgan et al. |
| 2016/0262736 A1 | 9/2016 | Ross et al. |
| 2016/0262745 A1 | 9/2016 | Morgan et al. |
| 2016/0293055 A1 | 10/2016 | Hofstetter |
| 2016/0296144 A1 | 10/2016 | Gaddam et al. |

FOREIGN PATENT DOCUMENTS

| | | |
|---|---|---|
| CN | 2909427 Y | 6/2007 |
| CN | 101313842 A | 12/2008 |
| CN | 201364679 Y | 12/2009 |
| CN | 201955979 U | 8/2011 |
| CN | 202443680 U | 9/2012 |
| CN | 202563792 U | 11/2012 |
| CN | 202601055 U | 12/2012 |
| CN | 202694651 U | 1/2013 |
| CN | 103050040 A | 4/2013 |
| CN | 203013103 U | 6/2013 |
| CN | 203038549 U | 7/2013 |
| CN | 203338651 U | 12/2013 |
| CN | 203397593 U | 1/2014 |
| CN | 203562128 U | 4/2014 |
| CN | 10388679 A | 6/2014 |
| DE | 41 05 892 | 8/1992 |
| DE | 44 14 832 | 11/1995 |
| DE | 19716341 C2 | 9/2000 |
| EP | 1 024 173 | 8/2000 |
| FR | 2 691 826 | 12/1993 |
| FR | 2 917 876 | 12/2008 |
| FR | 2 917 876 A1 | 12/2008 |
| GB | 2488994 A | 9/2012 |
| JP | 10 211160 | 8/1998 |
| JP | 2001005378 A | 1/2001 |
| JP | 2009236963 A | 10/2009 |
| JP | 3162161 U | 8/2010 |
| JP | 2013127496 A | 6/2013 |
| MX | PA 02004422 A | 11/2003 |
| PT | 106230 | 9/2013 |
| WO | WO 94/06109 | 3/1994 |
| WO | WO 1994/06109 | 3/1994 |
| WO | WO 96/42076 | 2/1996 |
| WO | WO 1996/042076 | 2/1996 |
| WO | WO 98/58358 | 12/1998 |
| WO | WO 1998/58358 | 12/1998 |
| WO | WO 1999/01074 A1 | 1/1999 |
| WO | WO 2000/36577 | 6/2000 |
| WO | WO/2002/38039 A2 | 5/2002 |
| WO | WO 2002/038039 A3 | 5/2002 |
| WO | WO 2004/032095 | 4/2004 |
| WO | WO 2004/082486 A1 | 9/2004 |
| WO | WO 2005/071639 A1 | 8/2005 |
| WO | WO 2006/083963 A2 | 8/2006 |
| WO | WO 2007/068360 | 6/2007 |
| WO | WO 2008/021720 | 2/2008 |
| WO | WO 2009/000939 | 12/2008 |
| WO | 2010/094730 | 8/2010 |
| WO | WO 2010/094730 | 8/2010 |
| WO | WO 2011/035410 A1 | 3/2011 |
| WO | WO 2011/046606 A1 | 4/2011 |
| WO | WO 2011/151304 A1 | 12/2011 |
| WO | WO 2012/149606 A1 | 11/2012 |
| WO | WO 2012/168287 A1 | 12/2012 |
| WO | WO 2012/175993 | 12/2012 |
| WO | WO 2013/048978 A1 | 4/2013 |
| WO | WO 2013/103956 A1 | 7/2013 |
| WO | WO 2014/022815 A1 | 2/2014 |
| WO | WO 2014/093669 A1 | 6/2014 |
| WO | WO 2015/148817 A1 | 10/2015 |
| WO | WO 2016/183412 A1 | 11/2016 |

OTHER PUBLICATIONS

International Bureau of WIPO, International Preliminary Report on Patentability for International Application No. PCT/US2012/070971, titled "Advanced Surgical Simulation" dated Jun. 24, 2014.

International Bureau of WIPO, International Preliminary Report on Patentability for International Application No. PCT/US2012/060997, titled "Simulated Tissue Structure For Surgical Training" dated Apr. 22, 2014.

The International Bureau of WIPO, International Preliminary Report on Patentability for International Application No. PCT/US2016/018697, entitled "Simulated Tissue Structures and Methods," dated Aug. 31, 2017, 14 pgs.

European Patent Office, The International Search Report and Written Opinion for International Application No. PCT/US2018/018895, entitled "Synthetic Tissue Structures for Electrosurgical Training and Simulation," dated May 17, 2018, 12 pgs.

The International Bureau of WIPO, International Preliminary Report on Patentability for International Application No. PCT/US2016/062669, entitled "Simulated Dissectible Tissue," dated May 31, 2018, 11 pgs.

European Patent Office, Invitation to Pay Additional Fees for International Application No. PCT/US2016/062669, titled "Simulated Dissectible Tissue", dated Feb. 10, 2017, 8 pgs.

European Patent Office, The International Search Report and Written Opinion of the International Searching Authority for International Application No. PCT/US2016/055148 titled "Hysterectomy Model", dated Feb. 28, 2017, 12 pgs.

The International Bureau of WIPO, International Preliminary Report on Patentability, for PCT application No. PCT/US2013/053497, titled, Simulated Stapling and Energy Based Ligation for Surgical Training, dated Feb. 12, 2015.

The International Bureau of WIPO, International Preliminary Report on Patentability for International Application No. PCT/US2015/020574, entitled "Advanced First Entry Model for Surgical Simulation," dated Sep. 22, 2016, 9 pgs.

European Patent Office, The International Search Report and Written Opinion of the International Searching Authority for International Application No. PCT/US2016/0043277 titled "Appendectomy Model", dated Oct. 4, 2016, 12 pgs.

The International Bureau of WIPO, International Preliminary Report on Patentability for International Application No. PCT/US2015/022774, titled "Simulated Dissectible Tissue," dated Oct. 6, 2016, 9 pgs.

European Patent Office, The International Search Report and Written Opinion of the International Searching Authority for International Application No. PCT/US2016/041852 titled "Simulated Dissectible Tissue", dated Oct. 13, 2016, 12 pgs.

European Patent Office, The International Search Report and Written Opinion for International Application No. PCT/US2012/070971, dated Mar. 18, 2013, titled "Advanced Surgical Simulation."

European Patent Office, The International Search Report and Written Opinion for International Application No. PCT/US2013/061728 dated Oct. 18, 2013, entitled "Surgical Training Model for Laparoscopic Procedures".

(56) References Cited

OTHER PUBLICATIONS

European Patent Office, The International Search Report and Written Opinion for International Application No. PCT/US2013/062363, dated Jan. 22, 2014, entitled Surgical Training Model for Laparoscopic Procedures.

European Patent Office, The International Search Report and Written Opinion for International Application No. PCT/US2013/061557, dated Feb. 10, 2014, entitled "Surgical Training Model for Laparoscopic Procedures."

European Patent Office, The International Search Report and Written Opinion for International Application No. PCT/US2013/061949, dated Feb. 17, 2014, entitled "Surgical Training Model for Laparoscopic Procedures."

European Patent Office, The International Search Report and Written Opinion for International Application No. PCT/US2013/062269, dated Feb. 17, 2014, entitled "Surgical Training Model for Transluminal Procedures."

The International Bureau of WIPO, International Preliminary Report on Patentability for International Application No. PCT/US2012/060997, titled "Simulated Tissue Structure for Surgical Training" dated Apr. 22, 2014.

The International Bureau of WIPO, International Preliminary Report on Patentability for International Application No. PCT/US2012/070971, titled "Advanced Surgical Simulation" dated Jun. 24, 2014.

European Patent Office, The International Search Report and Written Opinion for International Application No. PCT/US2014/019840 dated Jul. 4, 2014 entitled "Advanced Surgical Simulation Constructions and Methods."

European Patent Office, The International Search Report and Written Opinion of the International Searching Authority for International Application No. PCT/US2014/048027 titled "First Entry Model", dated Oct. 17, 2014.

European Patent Office, The International Search Report and Written Opinion of the International Searching Authority for International Application No. PCT/US2014/038195 titled "Hernia Model", dated Oct. 15, 2014.

Anonymous: Realsim Systems—LTS2000, Sep. 4, 2005, pp. 1-2, XP055096193, Retrieved from the Internet: URL:https://web.archive.org/web/2005090403;3030/http://www.realsimsystems.com/exersizes.htm (retrieved on Jan. 14, 2014).

The International Bureau of WIPO, International Preliminary Report on Patentability for international application No. PCT/US2013/061728, titled Surgical Training Model for Laparoscopic Procedures, dated Apr. 9, 2015.

The International Bureau of WIPO, International Preliminary Report on Patentability for International Application No. PCT/US2013/062363, titled Surgical Training Model for Laparoscopic Procedures, dated Apr. 9, 2015.

The International Bureau of WIPO, International Preliminary Report on Patentability for International Application No. PCT/US2013/062269, titled Surgical Training Model for Laparoscopic Procedures, dated Apr. 9, 2015.

The International Bureau of WIPO, International Preliminary Report on Patentability for International Application No. PCT/US2013/061557, titled Surgical Training Model for Laparoscopic Procedures, dated Apr. 9, 2015.

The International Bureau of WIPO, International Preliminary Report on Patentability for International Application No. PCT/US2013/061949, titled Surgical Training Model for Laparoscopic Procedures, dated Apr. 9, 2015.

European Patent Office, The International Search Report and Written Opinion for International Application No. PCT/US2014/042998, title; Gallbladder Model, dated Jan. 7, 2015.

European Patent Office, The International Search Report and Written Opinion for International Application No. PCT/US2015/020574, titled "Advanced First Entry Model for Surgical Simulation," dated Jun. 1, 2015.

European Patent Office, The International Search Report and Written Opinion for International Application No. PCT/US2015/022774, dated Jun. 11, 2015 entitled "Simulated Dissectible Tissue."

Simulab, Hernia Model, http://www.simulab.com/product/surgery/open/hernia model.

Limps and Things, EP Guildford MATTU Hernia Trainer, http://limbsandthings.com/us/products/tep-guildford-mattu-hernia-trainer/.

McGill Laparoscopic Inguinal Hernia Simulator, Novel Low-Cost Simulator for Laparoscopic Inguinal Hernia Repair.

University of Wisconsin-Madison Biomedical Engineering, Inguinal Hernia Model, http://bmedesign.engr.wisc.edu/projects/s10/hernia_model/.

Kurashima Y et al, "A tool for training and evaluation of Laparoscopic inguinal hernia repair; the Global Operative Assessment of Laparoscopic Skills-Groin Hernia" American Journal of Surgery, Paul Hoeber, New York, NY, US vol. 201, No. 1, Jan. 1, 2011, pp. 54-61 XP027558745.

Anonymous: Silicone rubber-from Wikipedia, the free encyclopedia, pp. 1-6, XP055192375, Retrieved from the Internet: URL:http://en.wikipedia.org/w.index.php?title=Silicone_rubber&oldid=596456058 (retrieved on May 29, 2015).

Lamouche, et al., "Review of tissue simulating phantoms with controllable optical, mechanical and structural properties for use in optical coherence tomography," Biomedical Optics Express, Jun. 1, 2012, 18 pgs., vol. 3, No. 6.

The International Bureau of WIPO, International Preliminary Report on Patentability for International Application No. PCT/US2014/019840, titled Simulated Tissue Structure for Surgical Training, dated Sep. 11, 2015.

The International Bureau of WIPO, International Preliminary Report on Patentability for International Application No. PCT/US2014/038195, titled Hernia Model, dated Nov. 26, 2015.

European Patent Office, International Search Report for International Application No. PCT/US2011/053859 A3, dated May 4, 2012, entitled "Portable Laparoscopic Trainer".

European Patent Office, The International Search Report and Written Opinion for International Application No. PCT/US2012/60997, dated Mar. 7, 2013, entitled "Simulated Tissue Structure for Surgical Training".

European Patent Office, The International Search Report and Written Opinion for International Application No. PCT/US2012/070971, dated Mar. 18, 2013, entitled "Advanced Surgical Simulation".

Human Patient Simulator, Medical Education Technologies, Inc., http://www.meti.com (1999) all.

The International Bureau of WIPO, International Preliminary Report on Patentability for International Application No. PCT/US2011/053859, titled "Portable Laparoscopic Trainer" dated Apr. 2, 2013.

The International Bureau of WIPO, International Preliminary Report on Patentability for International Application No. PCT/US2014/042998, titled "Gallbladder Model" dated Dec. 30, 2015.

The International Bureau of WIPO, International Preliminary Report on Patentability for International Application No. PCT/US2014/048027, titled "First Entry Model" dated Feb. 4, 2016.

The International Bureau of WIPO, International Preliminary Report on Patentability for International Application No. PCT/US2016/0032292, entitled "Synthetic Tissue Structures for Electrosurgical Training and Simulation," dated Nov. 23, 2017, 2017, 8 pgs.

The International Bureau of WIPO, International Preliminary Report on Patentability for International Application No. PCT/US2016/034591, entitled "Surgical Training Model for Laparoscopic Procedures," dated Dec. 7, 2017, 2017, 14 pgs.

European Patent Office, Examination Report for European Application No. 14733949.3 titled "Gallbladder Model," dated Dec. 21, 2016, 6 pgs.

European Patent Office, The International Search Report and Written Opinion of the International Searching Authority for International Application No. PCT/US2016/062669 titled "Simulated Dissectible Tissue," dated Apr. 5, 2017, 19 pgs.

European Patent Office, The International Search Report and Written Opinion of the International Searching Authority for Interna-

(56) References Cited

OTHER PUBLICATIONS tional Application No. PCT/US2017/020389 titled "Simulated Tissue Cartridge", dated May 24, 2017, 13 pgs.
The International Bureau of WIPO, International Preliminary Report on Patentability and Written Opinion for International Application No. PCT/US2015/059668, entitled "Simulated Tissue Models and Methods," dated May 26, 2017, 16 pgs.
Society of Laparoendoscopic Surgeons, "Future Technology Session: The Edge of Innovation in Surgery, Space, and Business" http://www.laparoscopytoday.com/endourology/page/2/ , Figure 1B: http://laparoscopy.blogs.com/laparoscopy_today/images/6-1/6-1VlaovicPicB.jpg , Sep. 5-8, 2007, 10 pgs.
Miyazaki Enterprises, "Miya Model Pelvic Surgery Training Model and Video," www.miyazakienterprises, printed Jul. 1, 2016, 1 pg.
European Patent Office, International Search Report and Written Opinion for International Application No. PCT/US2015/059668 titled "Simulated Tissue Models and Methods" dated Apr. 26, 2016, 20 pgs.
Australian Patent Office, Patent Examination Report No. 1 for Australian Application No. 2012358851 titled "Advanced Surgical Simulation" dated May 26, 2016, 3 pgs.
European Patent Office, International Search Report and Written Opinion for International Application No. PCT/US2016/032292 titled "Synthetic Tissue Structures for Electrosurgical Training and Simulation," dated Jul. 14, 2016, 11 pgs.
European Patent Office, International Search Report and Written Opinion for International Application No. PCT/US2016/018697 titled "Simulated Tissue Structures and Methods," dated Jul. 14, 2016, 21 pgs.
European Patent Office, International Search Report and Written Opinion for International Application No. PCT/US2016/034591 titled "Surgical Training Model for Laparoscopic Procedures," dated Aug. 8, 2016, 18 pgs.
European Patent Office, The International Search Report and Written Opinion of the International Searching Authority for International Application No. PCT/US2016/036664 titled "Hysterectomy Model", dated Aug. 19, 2016, 15 pgs.
3D-MED Corporation, "Validated Training Course for Laparoscopic Skills", https://www.3-dmed.com/sites/default/files/product-additional/product-spec/Validated%20Training%20Course%for%20Laparoscopic%Skills.dox_3.pdf , printed Aug. 23, 2016, pp. 1-6.
3D-MED Corporation, "Loops and Wire #1" https://www.3-dmed.com/product/loops-and-wire-1 , printed Aug. 23, 2016, 4 pgs.
Barrier, et al., "A Novel and Inexpensive Vaginal Hysterectomy Simulatory," Simulation in Healthcare: The Journal of the Society for Simulation in Healthcare, vol. 7, No. 6, Dec. 1, 2012, pp. 374-379.
European Patent Office, International Search Report and Written Opinion for International Application No. PCT/US2013/053497 titled "Simulated Stapling and Energy Based Ligation for Surgical Training" dated Nov. 5, 2013.
The International Bureau of WIPO, International Preliminary Report on Patentability for International Application No. PCT/US2016/036664, entitled "Hysterectomy Model," dated Dec. 21, 2017, 10 pgs.
The International Bureau of WIPO, International Preliminary Report on Patentability for International Application No. PCT/US2016/055148, entitled "Hysterectomy Model," dated Apr. 12, 2018, 12 pgs.
The International Bureau of WIPO, International Preliminary Report on Patentability for International Application No. PCT/US2016/041852, entitled "Simulated Dissectible Tissue," dated Jan. 25, 2018, 12 pgs.
European Patent Office, Extended European Search Report for European Patent Application No. EP 17202365.7, titled "Gallbladder Model", dated Jan. 31, 2018, 8 pgs.
The International Bureau of WIPO, International Preliminary Report on Patentability for International Application No. PCT/US2016/043277, entitled "Appendectomy Model," dated Feb. 1, 2018, 9 pgs.

\* cited by examiner

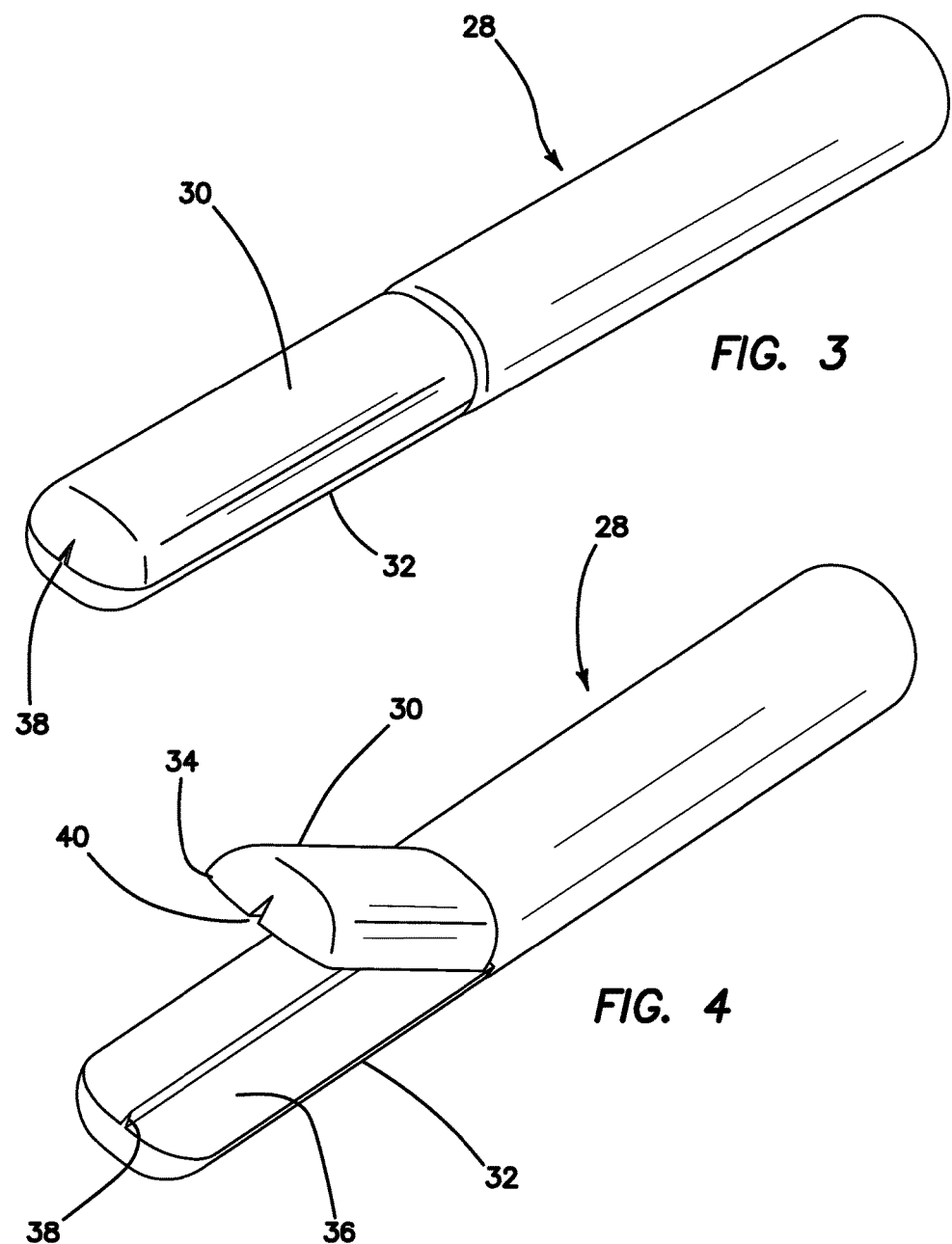

SIMULATED STAPLING AND ENERGY BASED LIGATION FOR SURGICAL TRAINING

CROSS-REFERENCE TO RELATED APPLICATION

This application claims priority to and benefit of U.S. Provisional Patent Application Ser. No. 61/679,494 entitled "Simulated stapling and energy based ligation for surgical training" filed on Aug. 3, 2012 which is incorporated herein by reference in its entirety.

FIELD OF THE INVENTION

The present invention is directed to medical training and simulation systems and devices that provide a user with visual, tactile and technical properties that emulate the situations extant in live surgical procedures.

BACKGROUND OF THE INVENTION

Several types of surgical devices are commonly used to cut and occlude tissue to control bleeding or leaking during or after dissection. These include surgical staplers, electrosurgical ligators, electrocautery instruments, blades, hooks, scissors and high frequency vibration ligators such as harmonic scalpels.

In particular, the linear surgical stapler is very useful and popular. The linear surgical stapler generally comprises an anvil surface against which staples are fired from an oppositely located cartridge. Tissue is captured in a gap between the jaw-like anvil and cartridge. A plurality of staples arranged in parallel rows in a staggered fashion is fired into the tissue and a blade operates to cut tissue between two sets of staple rows. Generally, the stapler is a single fire device and it must be reloaded with staple-cartridges during use. Most surgical procedures require the use of multiple cartridges. The stapler is designed to work only with a new staple cartridge in place and has a safety lock to prevent actuation of the blade if no new staple cartridge is present. The individual staple-cartridges are expensive. The cost may be justifiable for use in actual surgery but it is prohibitive in the case of training or practice.

Examples of energy-based surgical instruments include electrosurgical blades, probes, scissors, graspers, dissectors, electrocautery instruments and the like. Generally, electrosurgery is performed using an electrosurgical generator connected to an alternating current power supply and an instrument including one or more electrodes. Voltage is provided by the generator and high-frequency electric current is delivered to biological tissue through the electrode tip of the instrument or hand piece as a means to cut, coagulate, desiccate or fulgurate tissue. As the current is delivered, it passes through and heats the tissues to create the desired clinical effect. Alternatively, the electrical current is used to heat an instrument and a clinical effect is realized when the heated instrument is applied to tissue as in electrocautery. Additionally, many procedures make use of energy devices that are based on high frequency sound also known as ultrasound devices. These and other energy-based instruments advantageously provide a surgeon with the ability to make precise and nearly effortless cuts, dissect tissue with nearly instant thermal hemostasis limiting blood loss. Such instruments have become a standard within the surgical community and are used regularly in a variety of procedures.

Because of the effectiveness of electrosurgical and other energy-based instruments and procedures, it is important to train the clinician in the use of energy-based surgical instruments and procedures. Many of the existing training or simulating modules use live tissue from animals or cadavers. Real live tissue may be expensive and difficult to obtain, requires preservation using refrigeration and generates a smoke plume and odor when cauterized. With real tissue, a grounding plate is attached to an electrosurgical generator and the grounding plate is placed underneath the patient so that the current penetrates deeper into the tissues. In general, the practice of electrosurgical techniques using real tissue requires additional safety considerations. Since in the case of energy-based ligation, the devices are designed to operate only on conductive tissue, it is not always practical to use live tissue or cadaver in training or practice programs.

Therefore, there is a need to provide an inexpensive and practical way to train operators in the use of cutting and occlusion procedures such as surgical stapling and energy-based ligation. Also, there is a need to provide surgical training instruments that mimic the function of stapling and energy-based surgical instruments when used on elastomeric artificial tissue models.

SUMMARY OF THE INVENTION

According to one aspect of the invention, an inexpensive and practical training system to train operators in the use of surgical stapling and energy-based ligation procedures is provided. The system comprises a modified or simulated linear surgical stapling device having a fixed anvil and an opposed, movable jaw sized and configured to be closed upon subject tissue. A marking or inking element is associated with the jaw and anvil of the stapling device and configured to impose a visible pattern on the surfaces of subject tissue within the anvil and jaw. A pressure sensitive adhesive is associated with the inner surfaces of the simulated tissue that is activated upon compression between the anvil and jaw to simulate surgical occlusion.

According to another aspect of the invention, a surgical training system is provided. The system includes a simulated tissue structure comprising an outer surface, a first inner surface and a second inner surface adjacent to and at least partially facing the first inner surface. The system further includes a surgical training instrument having a first jaw and a second jaw connected to an elongate shaft such that at least one of the first jaw and second jaw is movable between an open position and a closed position with respect to the other one of the first jaw and second jaw. The first jaw has a first opposing surface and the second jaw has a second opposing surface. The elongate shaft is connected to a handle at a proximal end of the surgical training instrument. The handle is configured to manipulate at least one of the first jaw and the second jaw between the open position and the closed position. The surgical training instrument includes a blade configured to sever at least a portion of the simulated tissue structure placed between the first jaw and the second jaw to define a cut line in the simulated tissue structure. At least one of the first jaw and the second jaw includes a marking element configured to imprint markings on a portion of the outer surface of the simulated tissue structure placed between the first jaw and the second jaw when moved from the open position into contact with the simulated tissue structure in the closed position.

According to another aspect of the invention, a surgical training system is provided. The system includes a simulated tissue structure comprising an outer surface, a first inner surface and a second inner surface adjacent to and at least partially facing the first inner surface. The system further includes a surgical training instrument having a first jaw and a second jaw connected to an elongate shaft such that at least one of the first jaw and second jaw is movable between an open position and a closed position with respect to the other one of the first jaw and second jaw. The first jaw has a first opposing surface and the second jaw has a second opposing surface. The elongate shaft is connected to a handle at a proximal end of the surgical training instrument. The handle is configured to manipulate at least one of the first jaw and the second jaw between the open position and closed position. The surgical training instrument includes a blade configured to sever at least a portion of the simulated tissue structure placed between the first jaw and the second jaw to define a cut line in the simulated tissue structure. A portion of the first inner surface is joined to a portion of the second inner surface to form a predetermined pathway in the simulated tissue structure. The predetermined pathway having a width and a length.

According to another aspect of the invention, a surgical training system is provided. The system includes a simulated tissue structure comprising an outer surface, a first inner surface and a second inner surface adjacent to and at least partially facing the first inner surface. The system further includes a surgical training instrument having a first jaw and a second jaw connected to an elongate shaft such that at least one of the first jaw and second jaw is movable between an open position and a closed position with respect to the other one of the first jaw and the second jaw. The first jaw has a first opposing surface and the second jaw has a second opposing surface. The elongate shaft is connected to a handle at a proximal end of the surgical training instrument. The handle is configured to manipulate at least one of the first jaw and the second jaw between the open position and closed position. At least one of the first inner surface and the second inner surface includes adhesive and is separated from the other of the first inner surface and second inner surface. The simulated tissue structure is configured such that the closed position of the first jaw and the second jaw onto the simulated tissue structure positioned between the first jaw and the second jaw in the location of the adhesive compresses the first inner surface and the second inner surface together bringing the adhesive into contact with the other inner surface thereby bonding a portion of the first inner surface to a portion of the second inner surface to simulate surgical occlusion of the simulated tissue structure.

According to another aspect of the invention, a method for surgical training is provided. The method includes providing a simulated tissue structure comprising an outer surface, a first inner surface and a second inner surface adjacent to and at least partially facing the first inner surface. A portion of the first inner surface is joined to a portion of the second inner surface to form a predetermined pathway in the simulated tissue structure. The predetermined pathway has a width and a length. The method includes the step of providing a surgical training instrument having a blade. The blade of the surgical training instrument is placed within the width of the predetermined pathway. The simulated tissue structure is cut with the surgical training instrument along the length and within the width of the predetermined pathway.

According to another aspect of the invention, a method for surgical training is provided. The method includes the step of providing a simulated tissue structure comprising an outer surface, a first inner surface and a second inner surface adjacent to and at least partially facing the first inner surface. A region of at least one of the first inner surface and the second inner surface includes an adhesive. A surgical training instrument is provided. The surgical training instrument includes a first jaw and a second jaw connected to an elongate shaft such that at least one of the first jaw and second jaw is movable between an open position and a closed position with respect to the other one of the first jaw and second jaw. The first jaw has a first opposing surface and the second jaw has a second opposing surface. The elongate shaft is connected to a handle at a proximal end of the surgical training instrument. The handle is configured to manipulate at least one of the first jaw and the second jaw between the open position and closed position. The region of the at least one of the first inner surface and the second inner surface that includes adhesive is placed between the first jaw and the second jaw of the surgical training instrument with the first jaw and second jaw in the open position. The first jaw and the second jaw are moved from the open position to the closed position onto the region with adhesive. The simulated tissue structure is compressed between the first jaw and the second jaw in the region with adhesive. The first inner surface is adhered to the second inner surface by compressing the simulated tissue structure between the first jaw and the second jaw. The first jaw and the second jaw are moved from the closed position to the open position.

BRIEF DESCRIPTION OF THE DRAWINGS

FIG. 3 is a top perspective, partial view of a surgical training instrument with jaws in a closed orientation according to the present invention.

FIG. 4 is a top perspective, partial view of a surgical training instrument with jaws in an open orientation and according to the present invention.

DETAILED DESCRIPTION OF THE INVENTION

Figure 1:
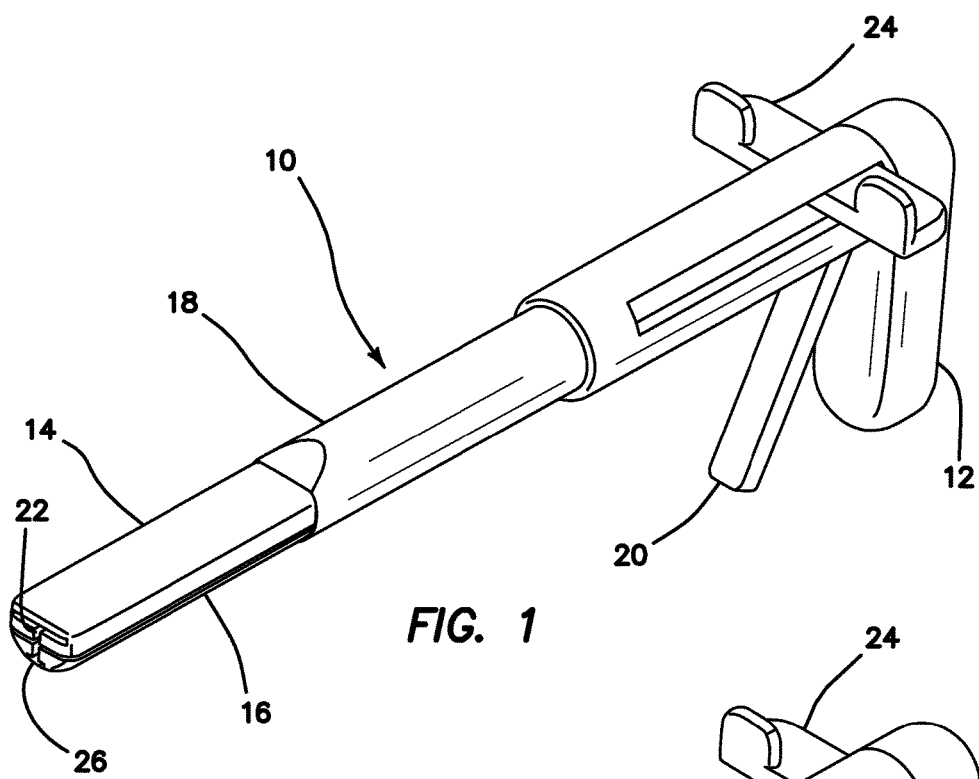
FIG. 1 is a top perspective view of a surgical training instrument with jaws in a closed orientation according to the present invention.
Figure 2:
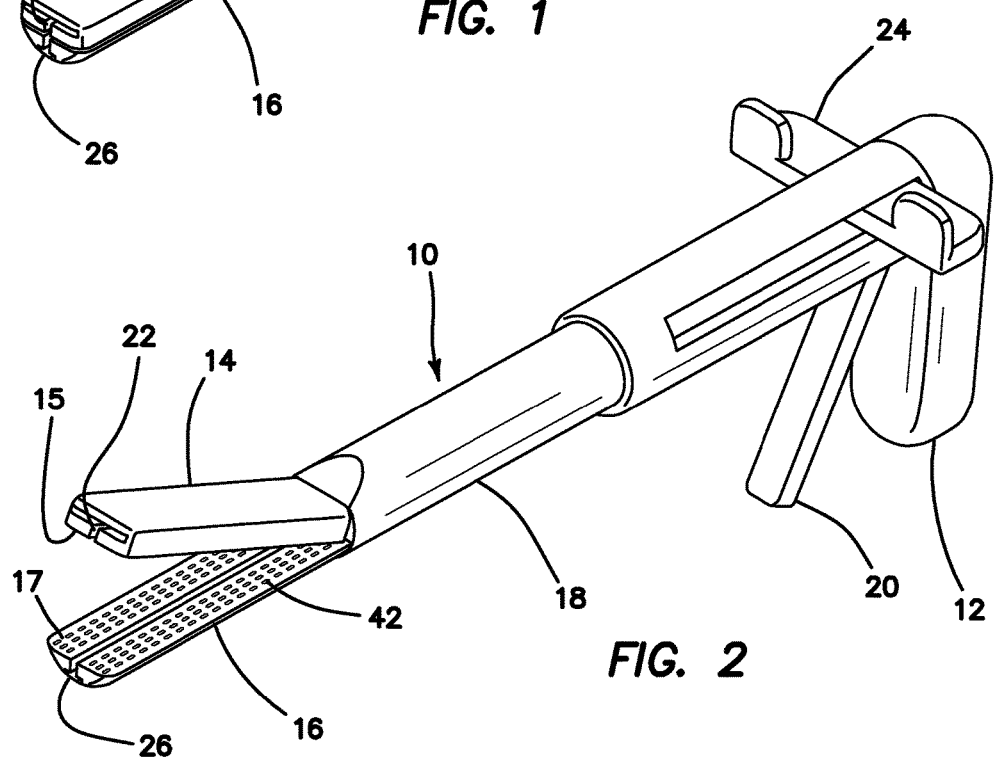
FIG. 2 is a top perspective view of a surgical training instrument with jaws in an open orientation according to the present invention.

Turning to FIGS. 1 and 2, a surgical training instrument 10 according to the present invention is shown. The surgical training instrument is a linear surgical stapler 10 apparatus comprises a handle 12 at a proximal end and two elongated jaw-like members, an upper jaw 14 and a lower jaw 16, at a distal end. An elongate shaft 18 extends between the handle 12 and the jaws 14, 16. The elongate shaft 18 houses an actuator shaft (not shown) that is mechanically connected to the handle 12 at the proximal end with gears such that movement of the trigger 20 moves the actuator shaft distally and proximally inside the elongate shaft 18. Such forth and back movement of the actuator shaft, permits the distal end of the actuator shaft to ramp in and out of a longitudinal slot 22 in one of the jaw-like members 14, 16. The longitudinal slot 22 is shown in the upper jaw 14 and advancement of the distal end of the actuator shaft into the longitudinal slot 22 articulates the upper jaw 14 into a closed orientation with respect to the lower jaw 16. The longitudinal slot 22 has a T-shape. Release of the trigger 20 retracts the actuator shaft from the longitudinal slot 22 allowing the upper jaw 14 to open. The upper jaw 14 is biased with a spring in the open position. The user can close and open the jaws 14, 16 by pulling and releasing the trigger 20 until the jaws 14, 16 are closed to capture simulated tissue at a desired location. With the jaws 14, 16 in a closed orientation, advancement of a lever 24 pushes the actuator shaft along the longitudinal slot 22 to the distal end of the jaws 14, 16. A complementary longitudinal slot 26 is formed in the lower jaw 16 and the distal end of the actuator shaft slides along the length inside the longitudinal slots 22, 26 of the closed jaws 14, 16. The longitudinal slot 26 of the lower jaw 16 is T-shaped. With the jaws 14, 16 closed, the longitudinal slots 22, 26 form an I-shape which is complementary in shape to an I-beam of the distal end of the actuator shaft. This configuration assists in keeping the jaws 14, 16 in the closed configuration. The distal end of the actuator shaft includes a cutting element or blade (not shown) that cuts simulated tissue along the longitudinal axis of the jaw 14, 16 as the actuator shaft is moved distally. In one variation, instead of pushing lever 24 distally to actuate the blade, the trigger 20 is configured to move the actuator distally after release of a safety button such that the trigger 20 can be pulled all way proximally without hindrance. The lever 24 is also used to retract the blade by pulling the lever 24 proximally.

Turning now to FIGS. 3-4, there is shown another variation for incorporating a cutting element or blade in a surgical training instrument 10 such as a simulated linear stapler 10 or simulated energy-based ligation tool. The simulated tool or stapler 28 of FIGS. 3-4 includes movable jaws 30, 32 similar to the jaws 14, 16 shown in FIGS. 1-2. Each of the opposing jaws 30, 32 comprise an opposing surface 34, 36, respectively. These opposing surfaces 34, 36 are substantially flat and together provide a compressive force onto simulated tissue material captured between the jaws 30, 32 when the jaws 30, 32 are in a closed orientation. A cutting element 38 is included in one of the jaws 30, 32 and is shown in FIG. 4 to be associated with the lower jaw 32. The cutting element 38 is a blade or other protrusion that is sufficiently capable of severing simulated tissue material. The cutting element 38 protrudes upwardly from the opposing surface 36 and extends longitudinally along the center line of the lower jaw 32. A slot 40 is included in the opposing surface 34 of the upper jaw 30 directly opposite from the cutting element 38. The slot 40 extends longitudinally along the center line of the upper jaw 30 and is sized and configured to receive at least part of the cutting element 38. The configuration of the cutting element 38 and slot 40 is such that material compressed between the jaws 30, 32 is severed upon compression or closure of the jaws 30, 32. The proximal end of the tool 28, comprising a handle and actuators, is not shown in FIGS. 3-4 but are described with respect to FIGS. 1-2. Other variations known to a person having ordinary skill in the art to make the jaws open and close, lock and sever simulated tissue material captured within the jaws 14, 16 are within the scope of the present invention.

Referring back to FIGS. 1-2 and with continued reference to FIGS. 3-4, the jaw-like members 14, 16, 30, 32 articulate relative to each other to open and close to capture material such as simulated tissue material between the jaw-like members 14, 16, 30, 32. The user controls the device 10 from the handle 12 to open and close the jaw-like members 14, 16, 30, 32 and, in general, manipulate and control the device 10. In a real surgical stapler, one of the jaw members carries a disposable cartridge containing staplers arranged in two or more rows. The other one of the jaw-like members comprises an anvil against which the staples are driven to deform the staple legs. Staples are driven out of the cartridge by a camming surface or slider that moves longitudinally against a plurality of laterally positioned pushers that push each staple out of the cartridge individually. Surgical staplers typically include a blade that follows the camming surface so as to cut the tissue between the two or more rows of delivered staples.

Figure 5:
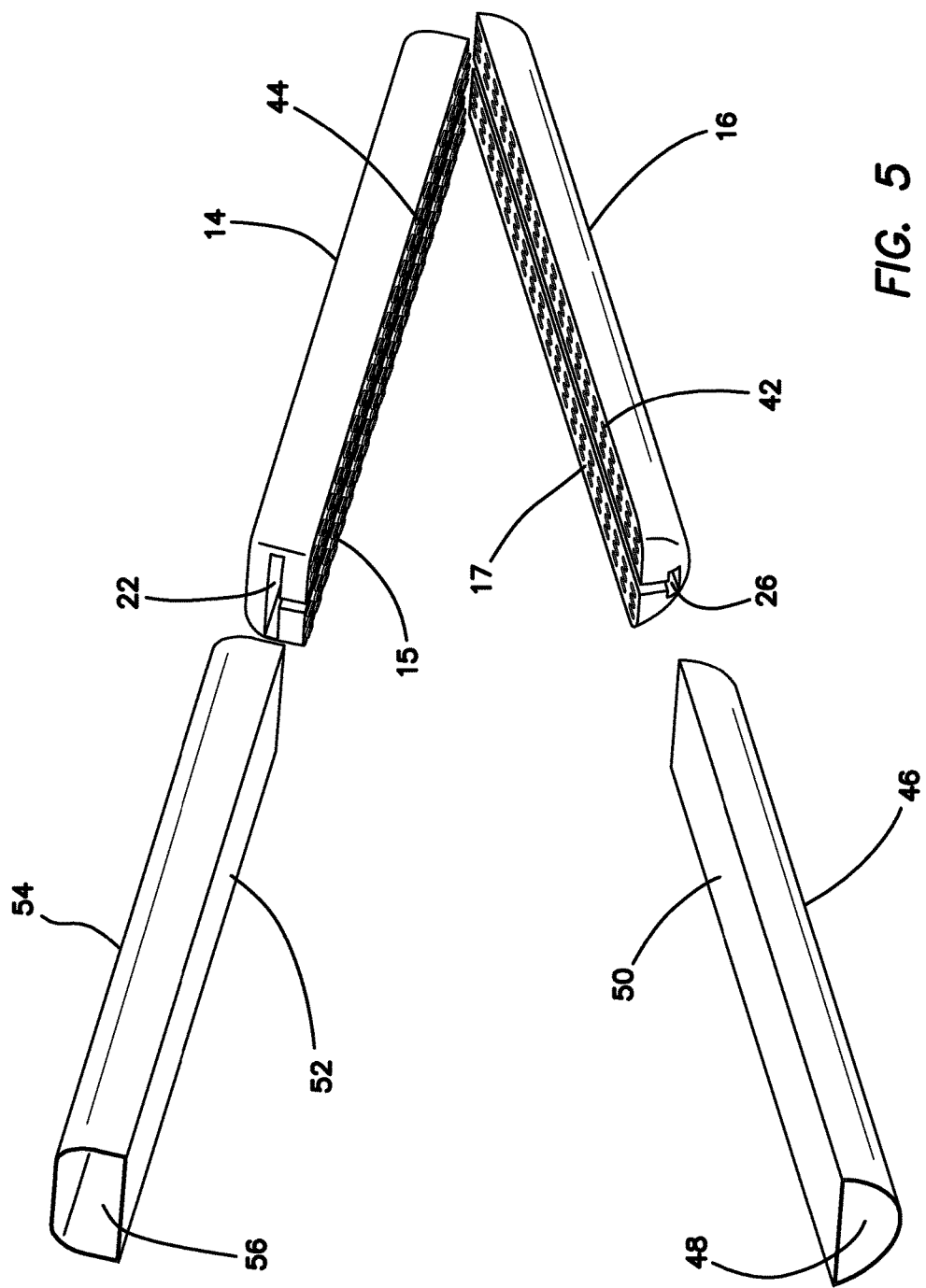
FIG. 5 is a perspective, partial view of a surgical training instrument with two marking elements and jaws in an open orientation according to the present invention.
Figure 6:
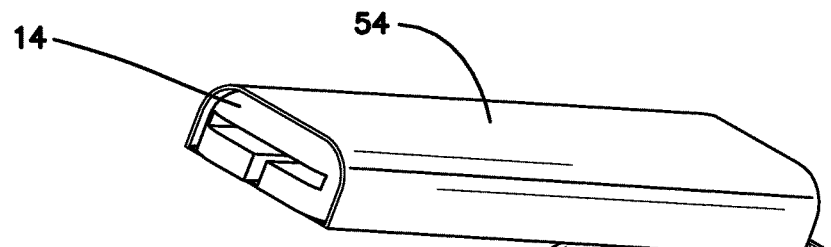
FIG. 6 is a perspective, partial view of a surgical training instrument with two marking elements placed on the jaws in an open orientation according to the present invention.

In the present invention, the surgical training instrument in the form of a linear stapler 10 does not carry any staples as the staple cartridges are expensive. Instead, the upper jaw 14 includes a planar opposing surface 15 that is made to resemble the anvil surface of a real stapler. In a real surgical linear stapler, the anvil surface is configured to properly deform staples that would exit from openings in the staple cartridge. The lower jaw 16 includes a planar opposing surface 17 that resembles a staple cartridge and may comprise an actual staple cartridge from a real linear stapler without the staples. All of the surgical training instruments of the present invention comprise a modified or simulated surgical instrument adapted for training purposes. The planar surface 17 of the lower jaw 16 is opposite from the opposing surface 15 of the upper jaw 14. The opposing surface 15 of the upper jaw 14 is marked, textured or embossed to replicate the appearance and position of multiple rows of an anvil surface having a plurality of staple pockets. Replicated staple pockets comprising concave indentations are provided in the opposing surface 15. In one variation, the staple pockets comprise convex protrusions configured to lift and/or carry and transfer ink or other marking compound in order to create realistic markings of staple deployment on one or more sides of the simulated tissue structure. A real staple cartridge houses a plurality of staples and includes exit openings in the opposing surface of the lower jaw. In the simulated stapler 10 of the present invention, the opposing surface 17 of the lower jaw 16 is marked, textured or embossed to replicate the appearance and position of multiple rows of staple exit openings. The opposing surface 17 of the lower jaw 16 may include small openings that replicate openings through which staples are ejected and exit the cartridge. In another variation, the opposing surface 17 includes raised portions in the location of real staple exit opening configured to impart the other side of the simulated tissue structure with markings and, as such, is configured to lift and/or carry and transfer ink or other marking compound. Typically, one or more rows of replicated exit openings 42, whether in the form of openings or protrusions in the opposing surface 17 of the lower jaw 16 on each side of the longitudinal slot 26, is provided. Three rows of replicated exit openings 42 on either side of the longitudinal slot 26 are shown in FIGS. 2, 5 and 6. Generally, the rows of replicated exit openings 42 are staggered with respect to adjacent rows. The opposing surface 15 of the upper jaw 14 includes replicated anvil pockets 44 that are visible in FIG. 5. The replicated anvil pockets 44 are arranged in at least one row on either side of the longitudinal slot 22 of the upper jaw 14. Typically, the replicated anvil pockets 44 are aligned directly opposite from the replicated exit openings 42 and are formed in rows that are staggered with respect to adjacent rows. Three rows of replicated anvil pockets 44 on either side of the longitudinal slot 22 are shown in FIG. 5. At least one of the opposing surfaces 15, 17 includes texture or embossments that are formed in plastic, metal, rubber or other material such that the texture or embossments in the location of replicated exit openings 42 and/or replicated anvil pockets 44 are raised or depressed from the planar opposing surfaces 15, 17.

When closed, the upper opposing surface 15 and the lower opposing surface 17 are configured to compress material, typically material simulating tissue such as silicone, plastic, thermoplastic elastomer or other material, between the jaws 14, 16, 30, 32. The texturing or embossment on one or more of the opposing surfaces 15, 17, 34, 36 leave a three-dimensional imprint in the simulated tissue material that mimics real rows of staples delivered in the simulated tissue material that is visible to the user. Also, these raised locations may be provided with ink, dye, or other material or marking compound having transferable color. At least one of the opposing surfaces 15, 17, 34, 36 of the upper and lower jaws 14, 16, 30, 32 respectively, may be compressed upon an inking pad prior to contact with simulated tissue material. This action will deposit a marking fluid, ink, dye, paste or powder upon the marking element comprising textured surfaces 15, 17, 34, 36 and when the jaws 14, 16, 30, 32 are closed down upon simulated tissue material, the markings will be transferred to the simulated tissue material leaving behind a realistic staple-like imprint. An inking pad may also be integrally formed within at least one of the jaws 14, 16, 30, 32 containing a carrier for dye, ink or other marking compound. For example, the carrier may comprise an ink cartridge, sponge or inking pad. The marking element is not limited to that shown in FIGS. 5-6 and may comprise any surface integral or not with the surgical training instrument that is configured to carry a marking compound and to release the marking compound in a pattern upon contact with the outer surface of the simulated tissue structure. Whereas the embossments would leave a three-dimensional imprint upon the simulated tissue material, the present invention is not so limited and the embossments, in particular, raised portions of either or both opposing surfaces 15, 17, 34, 36 are configured to leave a two-dimensional deposit of ink or other marking compound on the simulated tissue material without physically deforming the simulated tissue material. Of course, both a three-dimensional marking and color imprint or transfer of dye and the like upon the outer surface of the simulated tissue structure are within the scope of the present invention.

According to another aspect of the invention, an inking pad or sponge is provided. The inking pad or sponge is contained within a non-permeable container that is sized and configured to receive and direct a surgical training instrument 10. The container comprises a first portion containing an inking element such as a pad or sponge. A second portion of the container receives an instrument in a preferred orientation that facilitates presentation of the surfaces to be treated to the inking element. A third portion seals the container when not in use. The first portion is generally enlarged relative to the second portion and generally flat so that the marking element is held in a planar orientation. The second portion is configured so that an instrument inserted into the second portion approaches the inking element with the surfaces to be inked aligned with the flat surfaces of the inking element. The second portion is tubular or obliquely tubular so that the inserted surgical training instrument 10 is inserted with marking structures slightly separated for presentation to the inking element. For example, a linear stapler is inserted into the second portion with jaws open or slightly open and moved into the first portion where the jaws are subsequently closed upon the inking element transferring ink, dye or other marking compound to the jaws. If both jaws are to be inked then the inking pad or sponge is a double-sided pad or sponge that transfers ink from two oppositely disposed sides of the pad with one side contacting the first jaw and the other side of the pad contacting the second jaw when the jaws are closed down upon the inking pad. The third portion comprises any number of closure elements such as a zip lock, hook-and-loop type fastener or other closing device. A kit comprises at least one surgical training instrument and ink pad. The kit may additionally comprise at least one simulated tissue structure with or without adhesive according to the present invention.

With reference to FIG. 5, a first marking element 46 is provided. The first marking element 46 is shaped and configured to slide over the lower jaw 16. The first marking element 46 is sleeve-like having an inner lumen 48 that receives the lower jaw 16. The first marking element 46 includes a planar surface 50 that includes a marking compound and is made of a material, such as a sponge-like material, that will exude the marking compound through specific regions that are arranged upon the marking element 46, the opposing surface 15 of the upper jaw 14, the opposing surface 17 of the lower jaw 16, or a planar surface 52 of a second marking element 54 if one is employed. A second marking element 54 is configured with a lumen 56 to slide over and fit on the upper jaw 14 in the same sleeve-like fashion as the first marking element 46 as shown in FIG. 5. The second marking element 54 may also be provided with a marking compound and configured to exude the marking compound through specific regions. These specific regions may be arranged upon the marking element 54, the opposing surface 17 of the lower jaw 16, the opposing surface 15 of the upper jaw 14 or on the planar surface 50 of a first marking element 46 if a first marking element 46 is employed. It is clear that at least one of the jaws 14, 16 is provided with a marking element. FIG. 6 illustrates two marking elements 46, 54 placed on the upper and lower jaws 14, 16, respectively. The marking elements 46, 54 may be removed and replaced in simulation of the replacement of staple cartridges in an actual surgical linear stapler. As mentioned above, multiple staple cartridges may be necessary to cut across a larger section of tissue and used staple cartridges would have to be removed and replaced with a new staple cartridge for continued firing. The present invention advantageously provides at least one marking element that would provide the practitioner using the simulated tissue stapler 10 with the same action as required in using a real linear surgical stapler. In particular, the first marking element 46 that is placed over the lower jaw 16 that simulates the staple cartridge would be the marking element 46 that would be removed and replaced. In one variation, that marking element 46 would be the ink-bearing element. The marking elements 46, 54 are configured to create a resulting visual impression in the simulated tissue or organ that mimics the end result of real stapling at the surgical site in color, texture and visual impression upon the user including the use of red or other-colored marking compound.

The present invention additionally comprises simulated tissue material and structures configured to function with the surgical training instrument 10 such as a linear stapler or other simulated tool, ligation, occluding, or cutting instrument 10. Simulated tissue material and structures include any adjacent tissue surfaces, body conduits, arteries, veins and hollow organs made of elastomeric materials such as silicone, vinyl, polyurethane or any other polymer. Some of the adjacent tissue surfaces, body conduits, arteries, veins, hollow organs, or other tissue structure may include other material or are made solely from other material such as nylon, polyester, cotton or the like. In one variation of the simulated tissue structure of the present invention, the inner surfaces or portions of inner surfaces, or portions of other surfaces such as adjacent surfaces of the simulated tissue material or structure such as conduits, arteries, veins, and hollow organs are supplied with or coated with an adhesive such as a pressure-sensitive adhesive or contact adhesive. Generally, the simulated tissue structure includes an outer surface, a first inner surface and a second inner surface. The second inner surface is adjacent to and faces, at least partially, the first inner surface. The adhesive is located on at least one of the first inner surface and the second inner surface. The adhesive remains adhered to one of the inner surfaces and not adhered to the other of the inner surface. The cavity or gap in the simulated tissue structure between the first inner surface and the second inner surface is not closed until the surgical training instrument is acted upon the region with adhesive. In particular, when the jaws are closed down upon the outer surface in the location of the adhesive region on the inner surface, the adhesive is activated to adhere the first inner surface to the second inner surface. The jaws bring the inner surfaces together, compress them and adheres the first inner surface to the second inner surface in the location of compression and adhesive simulating surgical occlusion. In the case where the simulated tissue structure defines a lumen, the first inner surface and the second inner surface are located on the inner surface of the lumen.

When the jaws 14, 16 of the surgical training instrument 10 or other simulated surgical tool are located on the desired simulated tissue location and the jaws 14, 16 are closed down upon the simulated tissue, the simulated tissue will be compressed between the opposing surfaces 15, 17. At least a portion of the adjacent facing surfaces of the simulated tissue or simulated tissue structure is provided with adhesive, such as pressure-sensitive adhesive, double-sided tape, or contact adhesive, in particular, in at least the location of surgically desired placement of the simulated tool 10. For example, the inner surfaces or portions of inners surfaces of conduits, arteries, veins and hollow organs that face each other are supplied with or coated with an adhesive such as a pressure-sensitive adhesive or a contact adhesive on at least one of the surfaces. A hollow simulated tissue structure includes an inner surface opposite from another inner surface. At least one of these surfaces is coated with adhesive for the purpose of attachment to the other of these surfaces. In use, when a hollow simulated tissue structure is compressed between the jaws 14, 16 of the surgical training instrument 10, the inner surfaces, supplied with adhesive, are forced into occlusion and are adhered together as would tissue that was stapled or welded by a linear surgical stapler, energy-based ligation instrument, or other surgical device. Alternatively, the simulated tissue structure is provided with attractive elements instead of adhesive-based elements. Examples of attractive elements include hook-and-loop type fasteners such as VELCRO®, magnets, or the like attached to walls of the simulated tissue structure.

An example of an adhesive for use in the present invention is Styrene Block Copolymer (SBC) containing rosin or other tackifiers that render a sensitive, tacky surface. Other alternate materials are materials that are formulated to stick to themselves under compression. For example, silicone rubber may be compounded or formulated to fuse under pressure in certain conditions. An additional material choice comprises a naturally sticky material such as KRATON® gel or the like with or without a non-sticky external coating or external surface.

Figure 7:
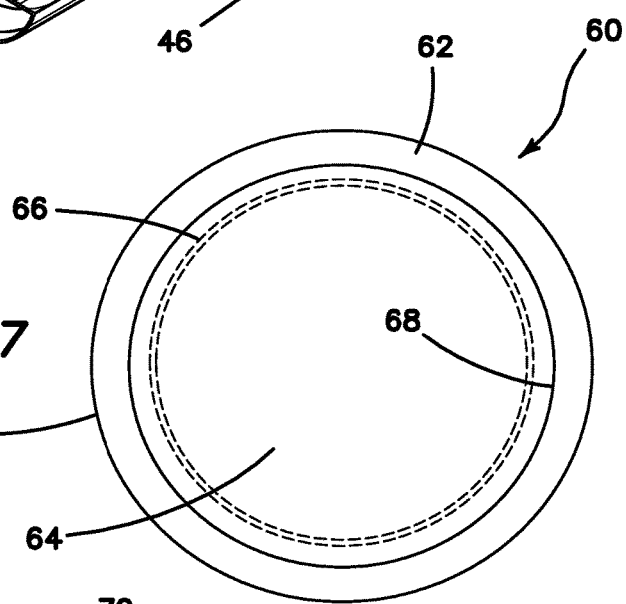
FIG. 7 is a cross-sectional view of a simulated tissue structure with adhesive according to the present invention.
Figure 8:
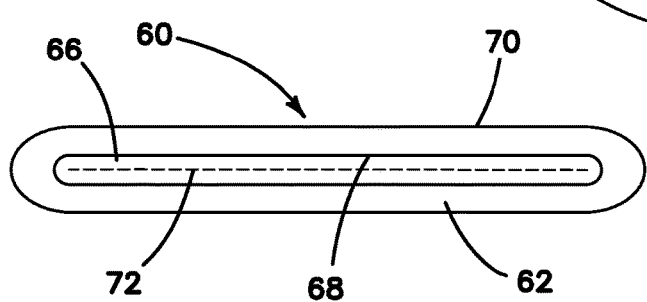
FIG. 8 is a cross-sectional view of a simulated tissue structure in a compressed configuration according to the present invention.

With reference to FIGS. 7-8, a simulated tissue structure 60 is shown in the shape of a hollow organ or body conduit. The simulated tissue structure 60 is an elastomeric and/or fabric structure having a wall 62 having an inner surface 68 and an outer surface 70. The simulated tissue structure 60 includes a lumen 64. An occlusive adhesive element 66 is provided on at least a portion of the internal surface or first inner surface along at least a portion of the length of the simulated tissue structure 60. The simulated tissue structure 60 is shown in FIG. 8 in a compressed configuration following a simulated surgical stapling or energy-based procedure showing the adherence of opposing adjacent surfaces along line 72. The compressed configuration of FIG. 8 is achieved by placing the jaws 14, 16, 30, 32 on a simulated tissue structure 60 and moving the jaws 14, 16, 30, 32 from an open position to a closed position squeezing the lumen 64 closed and into sealing engagement with itself.

Figure 9:
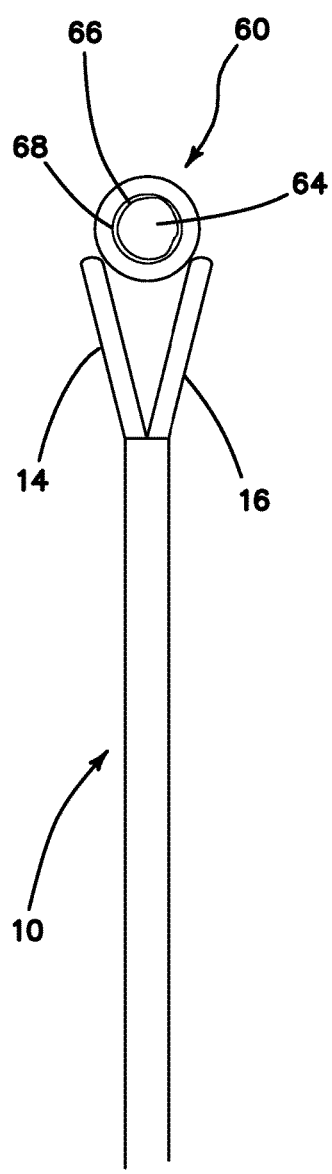
FIG. 9 is a cross-sectional view of a simulated tissue structure and a surgical training instrument in an open configuration according to the present invention.
Figure 10:
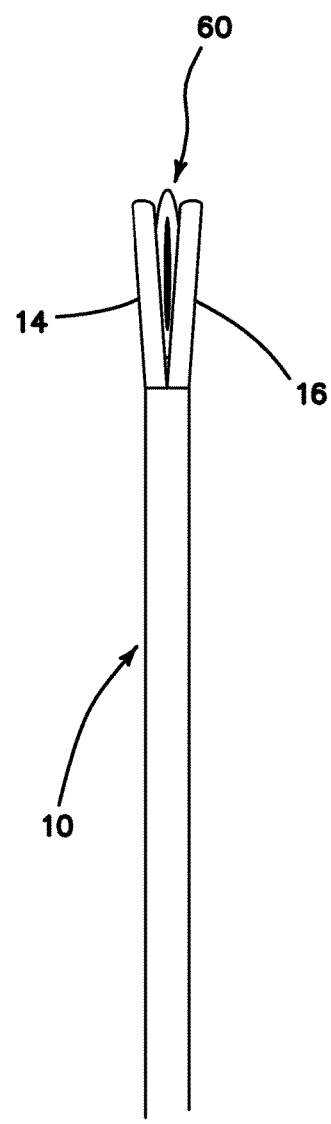
FIG. 10 is a cross-sectional view of a simulated tissue structure compressed inside a surgical training instrument in a closed configuration according to the present invention.
Figure 11:
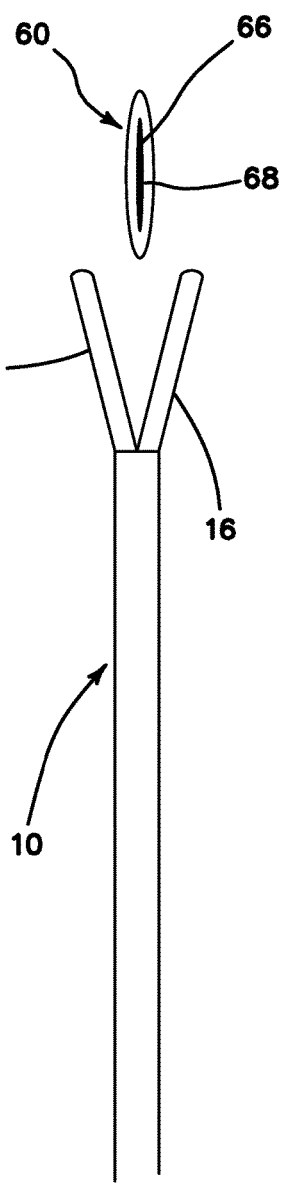
FIG. 11 is a cross-sectional view of a compressed simulated tissue structure and a surgical training instrument in an open configuration according to the present invention.

With reference to FIGS. 9-11, a surgical training instrument 10 according to the present invention such as a simulated energy-based grasper or dissector 10 is shown adjacent to a simulated tissue structure 60 shown in cross-section defining a lumen 64. The simulated tissue structure 60 is tubular in shape having a circular cross-section resembling a body conduit such as an artery or vein or other hollow organ. An inner surface 68 of the simulated tissue structure 60 is provided with adhesive 66 on at least a portion of the inner surface 68. FIG. 9 shows the adhesive 66 placed circumferentially around the inner surface. The distal end of the simulated surgical instrument 10 is shown in FIGS. 9-11. The surgical training instrument 10 comprises a pair of opposed jaws 14, 16, 30, 32 as described above. The jaws 14, 16, 30, 32 are opened and located adjacent to a surgically desirable location at the simulated tissue structure 60. Once properly positioned, the handle 12 is manipulated to close the jaws 14, 16, 30, 32 on the simulated tissue structure 60 compressing the simulated tissue structure 60 between the jaws 14, 16, 30, 32 as shown in FIG. 10. If the simulated surgical instrument 10 includes a cutting element or blade it is activated to sever the simulated tissue structure in the desired location. The simulated tissue structure 10 has an adhesive 66 such as a pressure-sensitive contact adhesive within the lumen 64 so that upon compression and severance, the cut ends appear to have been treated with an energy-based, electro-surgical or electrocautery device or the like with markings, ink-based or otherwise, being imparted to the surface of the simulated tissue structure 60. The jaws 14, 16, 30, 32 are then manipulated at the handle 12 into an open orientation and the severed simulated tissue structure 60 is removed from the instrument 10 as shown in FIG. 11. The simulated tissue structure 60 remains compressed because of the adhesive being activated upon compression or juxtaposition of the adjacent opposing surfaces with at least one surface bearing adhesive for creating a closed lumen 64 as would result from a real occlusive surgical instrument.

Figure 12:
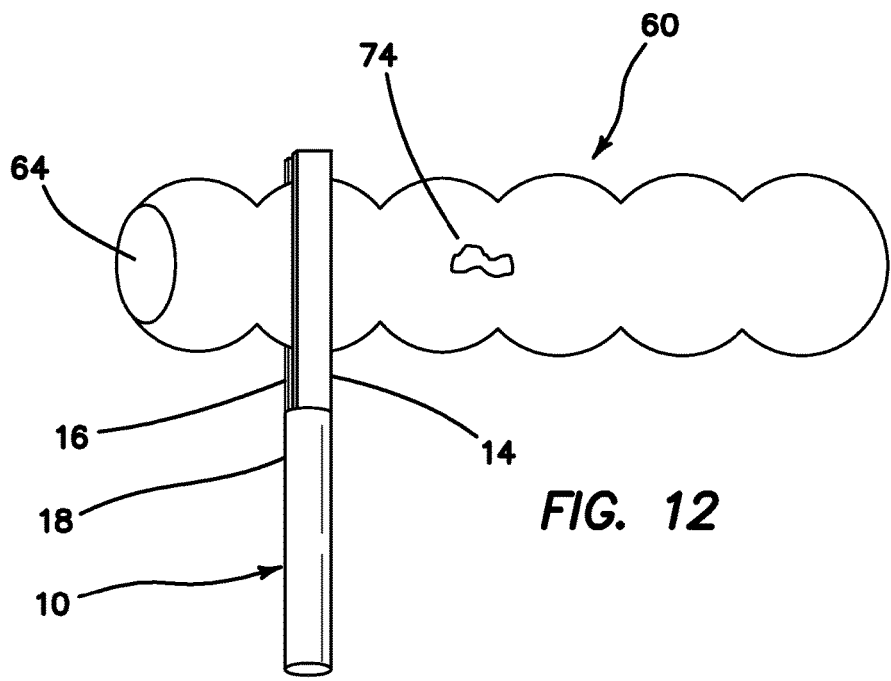
FIG. 12 is a top perspective view of a simulated tissue structure between jaws of a surgical training instrument positioned on one side of a lesion according to the present invention.
Figure 13:
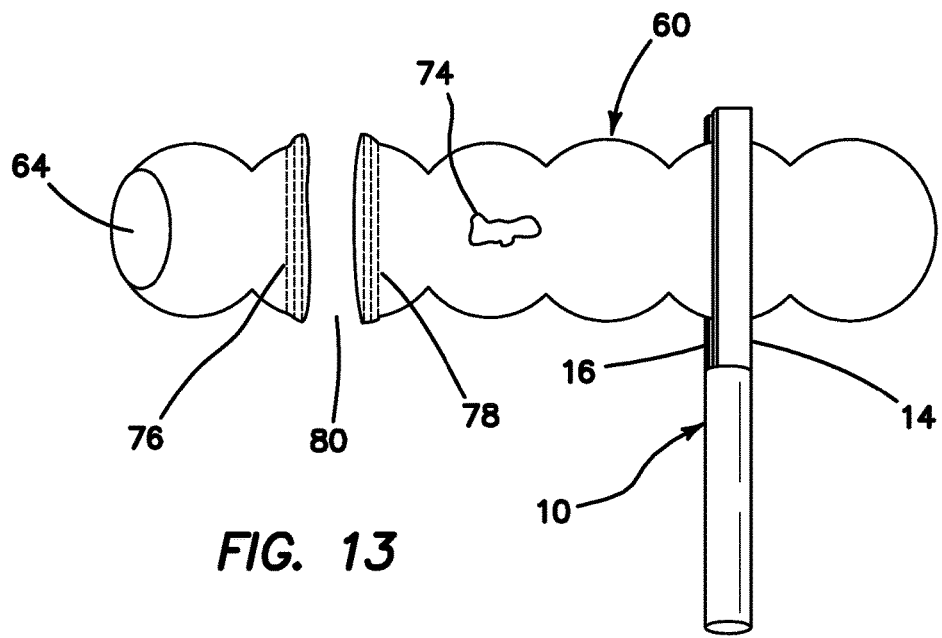
FIG. 13 is a top perspective view of a simulated tissue structure severed on one side of a lesion and jaws of a surgical training instrument positioned on another side of the lesion according to the present invention.

With reference to FIGS. 12-13, a simulated tissue structure 60 in the shape of a tubular body conduit is shown having a lesion 74 that is to be removed. The conduit is elongate and defines a lumen 64 wherein at least a portion of the inner surface of the conduit is provided with adhesive as described above. The adhesive may be selectively placed, for example, on either side of the tumor 74 or throughout the entirety of the inside of the lumen 64. In FIG. 12, a surgical training instrument 10 such as a stapler is shown with jaws 14, 16 closed upon a portion of the conduit 60. The simulated stapler 10 is operated to simulate the firing of staples by pulling the trigger 20 or advancing the lever 24 to advance a blade. If the surgical training instrument 28 of FIGS. 3-4 is used, the jaws 30, 32 are closed to a first closed position in which the cutting element 38 does not sever the simulated tissue 60 and then repositioned as needed to the desired location. To simulate stapling or cutting, the jaws 30, 32 are moved to a second closed position in which the simulated tissue is severed by the jaws 30, 32 coming sufficiently close together to engage the cutting element 38 in one jaw against the opposite jaw. After a simulated stapling, cutting, occlusion, or ligation, the jaws are opened and the simulated instrument 10 is removed leaving behind a plurality of simulated rows 76, 78 of staples which comprise a pattern of markings that resemble real staples. The pattern of markings are from ink, dye or other marking compound carried by the surgical training instrument 10 and imprinted upon or transferred to the outer surface of the simulated tissue structure 60 as shown in FIG. 13. Both sides of the simulated tissue structure 60 is marked in which both jaws are inked. Alternatively, only the side facing the user is marked in which only one of the jaws such as the top jaw is inked. Six rows of markings comprising three rows 76 on one side and three rows 78 on another side of the cut 80 are shown in FIG. 13. The markings may include not only color ink placement on the simulated tissue structure 60, but also, a three dimensional impression or embossment upon the simulated tissue structure 60 that mimic the raised and depressed areas of a real deployment of surgical staples. When the simulated stapler 10 is removed from the conduit 60, at least one of the marking elements 46, 54 is removed and replaced to simulate the reloading of a new and real staple cartridge. Alternatively, if the marking elements 46, 54 are not employed, the jaws are inked by compressing the jaws 14, 16 onto an ink pad to transfer ink to at least one of the jaws. The simulated stapler 10 is then reintroduced into the practice area, such as a laparoscopic trainer, and the jaws 14, 16 are placed in a second location at the other side of the lesion 74. The jaws 14, 16 are closed down by pulling of the trigger 20 and the simulated stapler 10 is activated again to mimic the firing of staples resulting in the simulated tissue 60 being cut in a second location leaving the similar pattern of ink markings on the simulated tissue 60 described above. The simulated tissue structure 60 that is located between the two cuts and containing the lesion 74 is removed. Compression of the simulated tissue structure 60 between the jaws has sealed the open lumen 64 closed in the location of the markings 76, 78 on either side of the cut 80 and also at the other side of the lesion 74 in the performance of a second cut.

Figure 14:
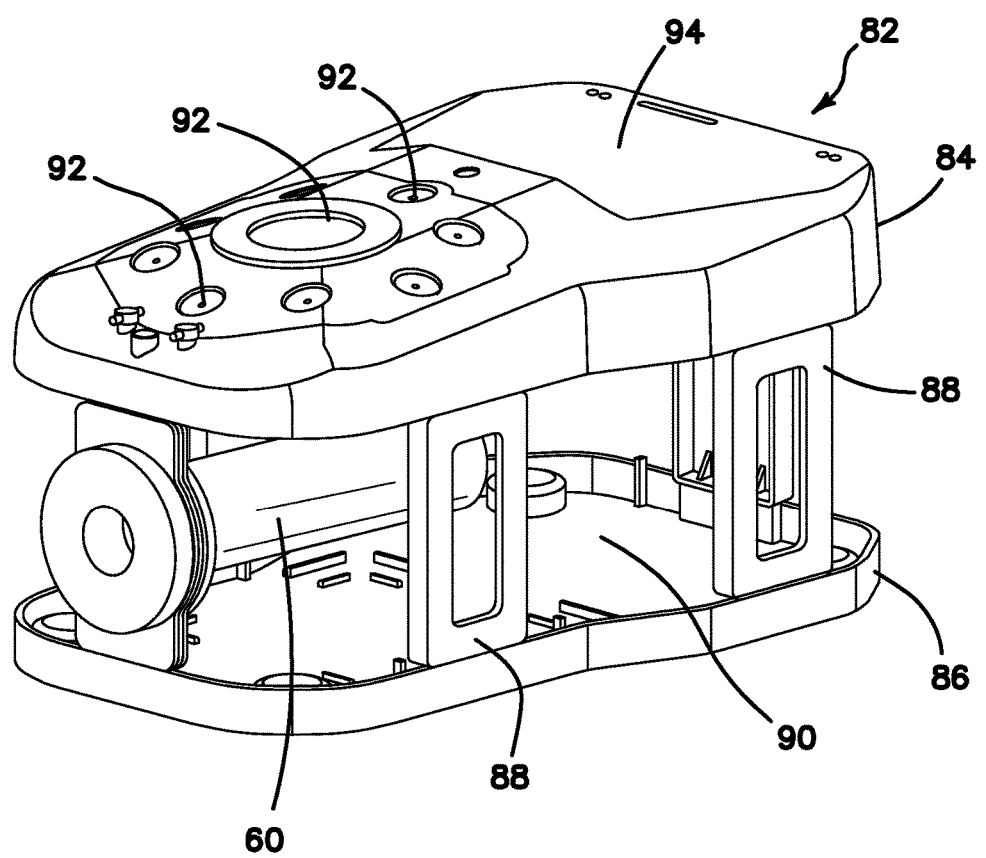
FIG. 14 is a top perspective view of laparoscopic trainer for use with a surgical training instrument and simulated tissue structure according to the present invention.

To perform any simulated surgical procedure, the simulated tissue structure 60 may be placed inside a laparoscopic trainer 82 such as the one depicted in FIG. 14 and described in co-pending U.S. patent application Ser. No. 13/248,449 entitled "Portable laparoscopic trainer" and filed on Sep. 29, 2011 by Pravong et al. to Applied Medical Resources Corporation and published as U.S. Patent Application Publication No. 2012/0082970, hereby incorporated by reference in its entirety herein. Other simulators and/or trainers may be used with the surgical training instruments and simulated tissue structures of the present invention.

A laparoscopic trainer 82 includes a top cover 84 connected to a base 86 by a plurality of legs 88 spacing the top cover 84 from the base 86. The laparoscopic trainer 82 is configured to mimic the torso of a patient such as the abdominal region. The top cover 84 is representative of the anterior surface of the patient and a space defined between the top cover 82 and the base 86 is representative of an interior of the patient or body cavity where organs reside. The laparoscopic trainer 82 is a useful tool for teaching, practicing and demonstrating various surgical procedures and their related instruments in simulation of a patient. For practicing various surgical techniques, surgical instruments such as the surgical training instrument 10 of the present invention are inserted into the cavity 90 of the laparoscopic trainer 20 through pre-established apertures 92 in the top cover 84. These pre-established apertures 92 may include seals that simulate trocars or may include simulated tissue that simulates the patient's skin and abdominal wall portions. Various tools and techniques may be used to penetrate the top cover 84 to perform mock procedures on simulated tissue structures 60 of the present invention placed between the top cover 84 and the base 86. An elongated conduit 60 is shown placed in the cavity 90 of the trainer 82 shown in FIG. 14. When placed inside the cavity 90 of the trainer 82, the simulated tissue structure 60 is generally obscured from the perspective of the user who can then practice performing surgical techniques laparoscopically by viewing the surgical site indirectly via a video feed displayed on a video monitor 94. The video display monitor 94 is hinged to the top cover 84 and is shown in a closed orientation in FIG. 14. The video monitor 94 is connectable to a variety of visual systems for delivering an image to the monitor 94. For example, a laparoscope inserted through one of the pre-established apertures 92 or a webcam located in the cavity 90 and used to observe the simulated procedure can be connected to the video monitor 94 and/or a mobile computing device to provide an image to the user.

Figure 15:
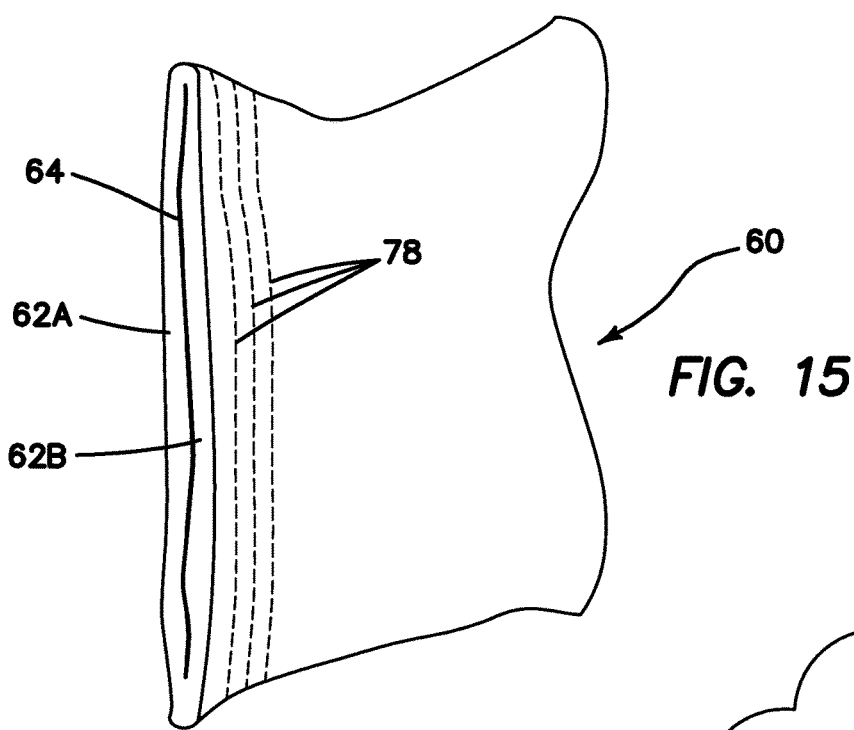
FIG. 15 is a top perspective view of a simulated tissue structure sealed and with markings at one end after being severed with a surgical training instrument according to the present invention.

FIG. 15 illustrates the final end condition of a portion of simulated tissue structure 60 that has the effects of being stapled by a linear stapler 10 described in a procedure shown in FIGS. 12-13 carried out in a laparoscopic trainer 82 or other simulator, for example, and removed. The surgical effects include a compressed lumen 64 in the location where two adjacent wall portions 62A, 62B are tightly approximated by the closure of jaws. The lumen 64 of the conduit 60 is closed and sealed by the adhesive. In the case of the present invention, the end condition is replicated or simulated without the use of real staples and what remains are markings from ink or dye and/or embossments or texturing from being compressed by the jaws 14, 16. As shown in FIG. 15, three rows of markings 78 resembling three rows of staples are adjacent to the cut line.

The simulated tissue 60 of the present invention advantageously permits the practice of a leak test to ensure that proper stapling or ligation has taken place. A leak test is performed by pumping air or other gas into the conduit 60 at one end and then applying water or other liquid such as saline solution at the cut line and along the markings 78 and observing to see if any bubbles are formed. If bubbles appear, then the practitioner knows that the conduit was not properly sealed by the ligation or stapling instrument. In this regard, adhesive applied to the inside of the lumen may be selectively applied to create the desired passing or failing of the leak test.

An elastomeric material is used as a body conduit or simulated tissue structure 60 having a lumen 64. Within the lumen 64 of the conduit 60, an adhesive such as a pressure-sensitive, contact adhesive is deposited or supplied so that upon compression of the elastomeric lumen 64, the adhesive is fully occluded and activated. The opposing walls 62A, 62B of the simulated conduit 60 are compressed, sealed and marked in a manner that appears to have been accomplished with a linear stapler employing real surgical staples or other occlusion device, thereby, simulating a surgical procedure.

Figure 16:
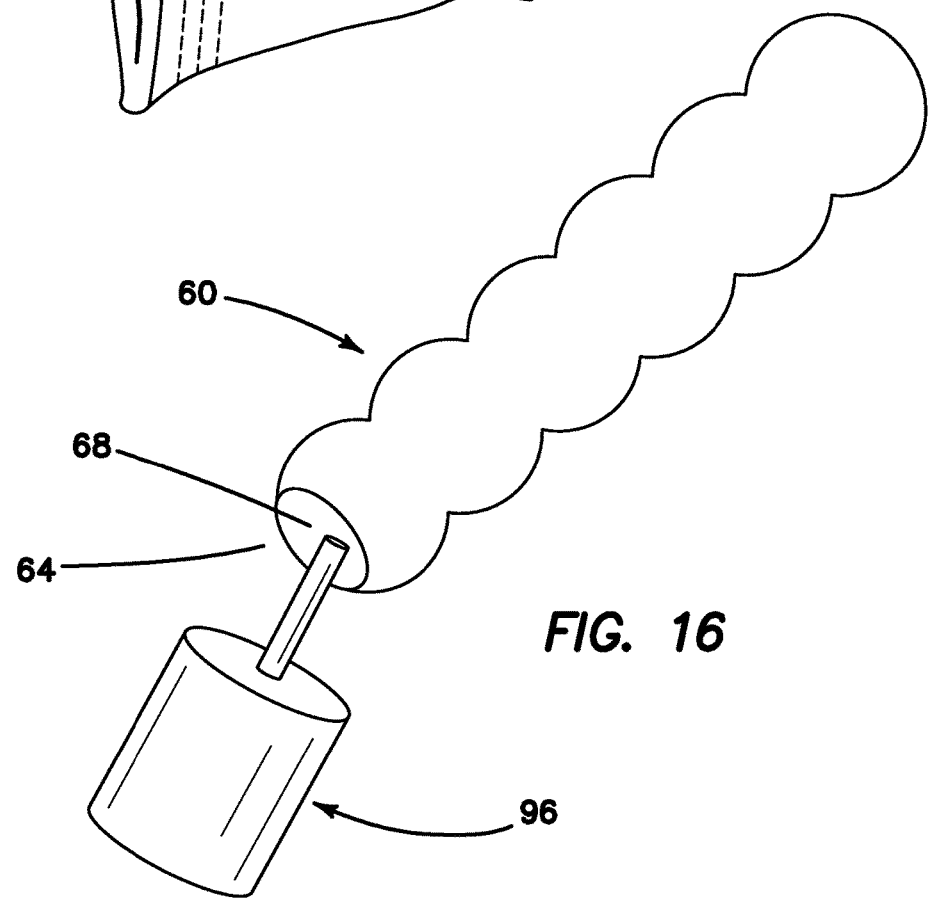
FIG. 16 is a top perspective view of adhesive being applied to a simulated tissue structure according to the present invention.
Figure 17:
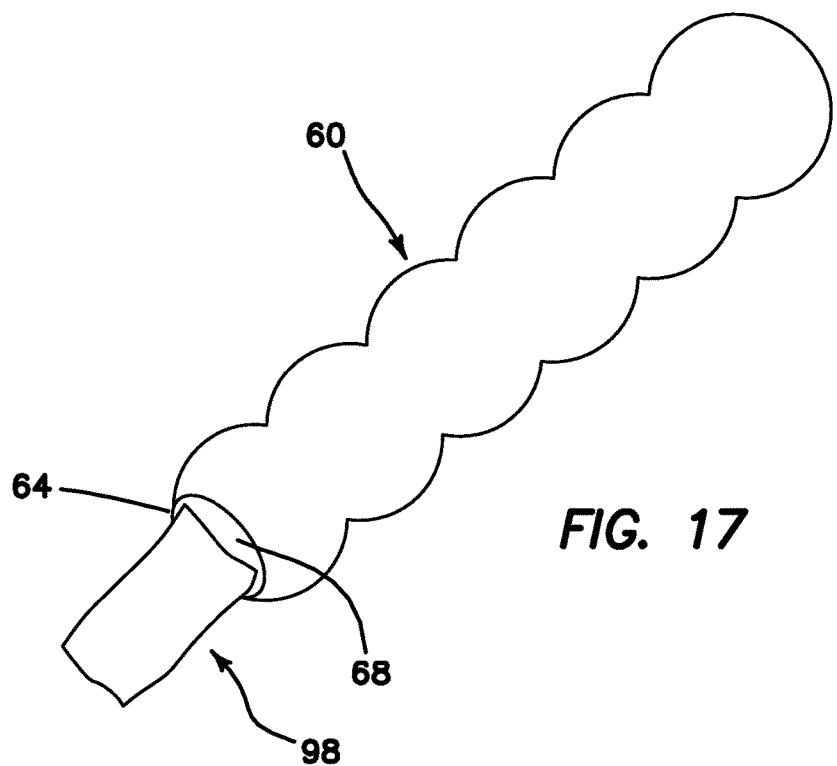
FIG. 17 is a top perspective view of adhesive being applied to a simulated tissue structure according to the present invention.
Figure 18:
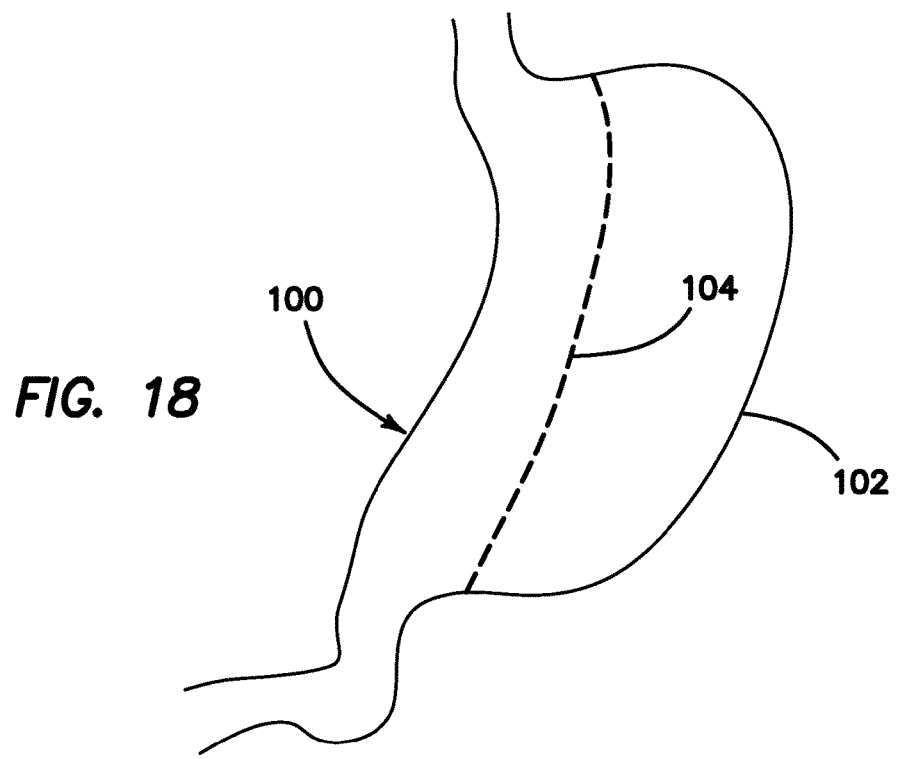
FIG. 18 is perspective view of a simulated tissue structure with a predetermined pathway according to the present invention.

With reference to FIGS. 16-17 a pressure-sensitive contact adhesive or element is placed within the lumen 64 of a simulated body conduit 10. It may be deposited upon the inner surface 68 using an adhesive applicator 96 or may comprise a wafer or strip layer 98 of double-sided material placed within the lumen 64.

Figure 19:
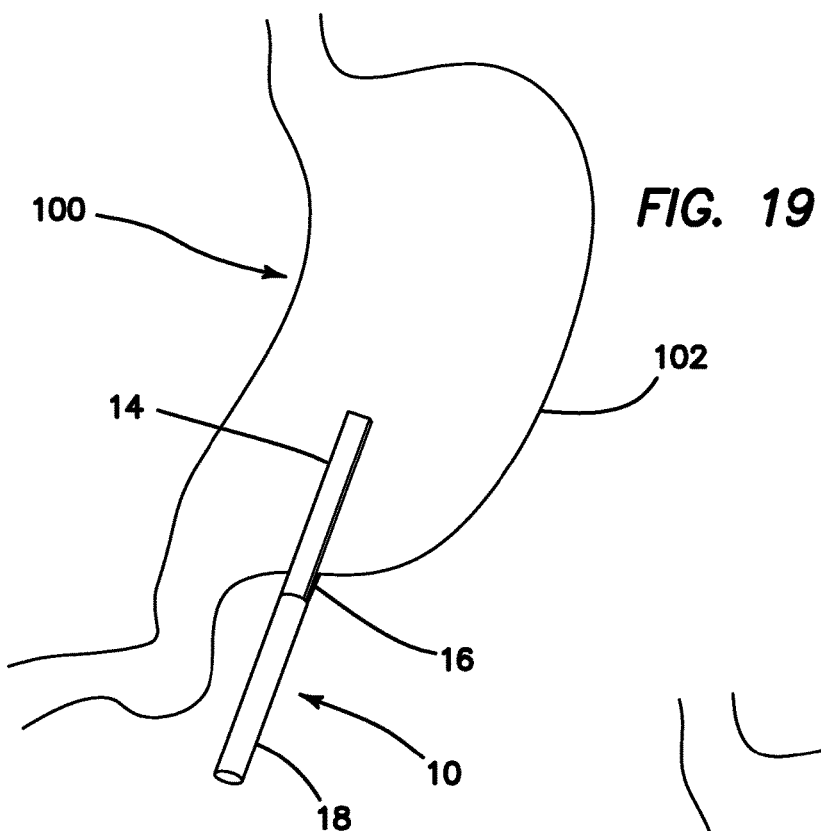
FIG. 19 is a perspective view of a surgical training instrument positioned on a simulated tissue structure according to the present invention.
Figure 20:
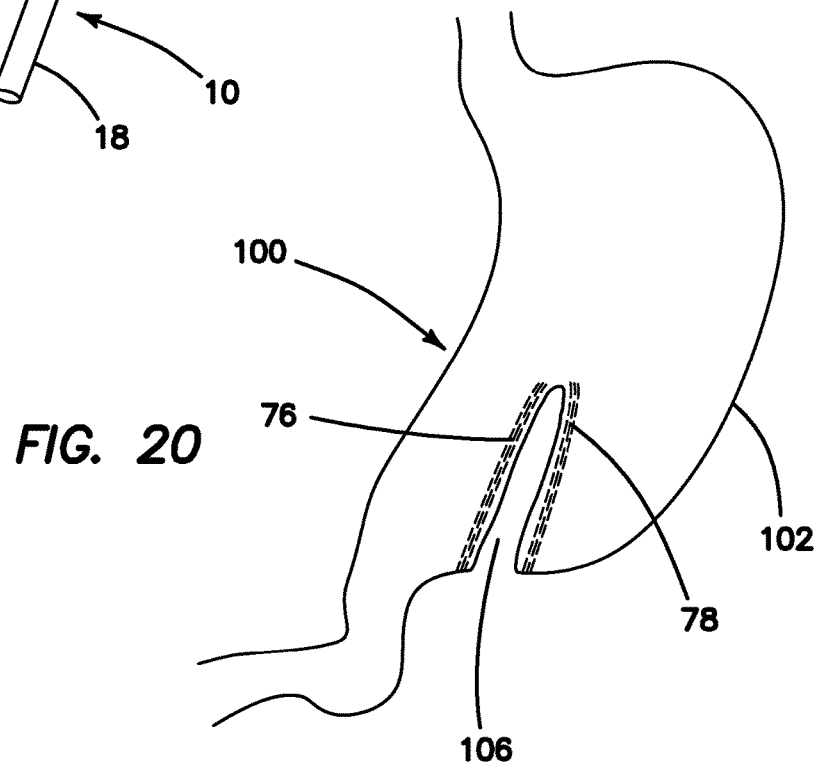
FIG. 20 is a perspective view of a simulated tissue structure with a cut and markings according to the present invention.
Figure 21:
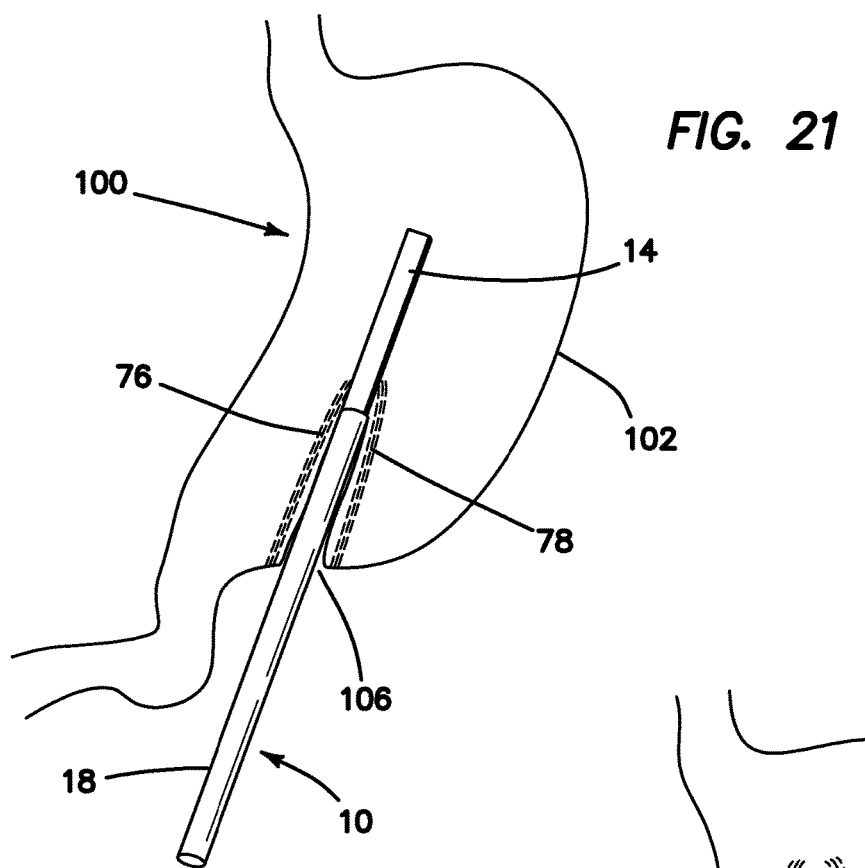
FIG. 21 is a perspective view of a surgical training instrument placed on a simulated tissue structure forward of a previous cut according to the present invention.
Figure 22:
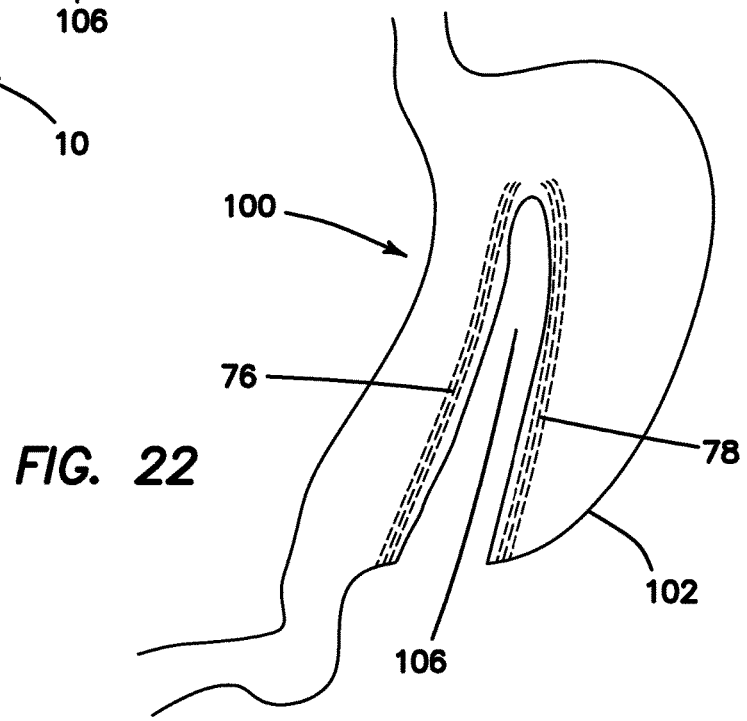
FIG. 22 is a perspective view of a simulated tissue structure with a longer cut and markings according to the present invention.
Figure 23:
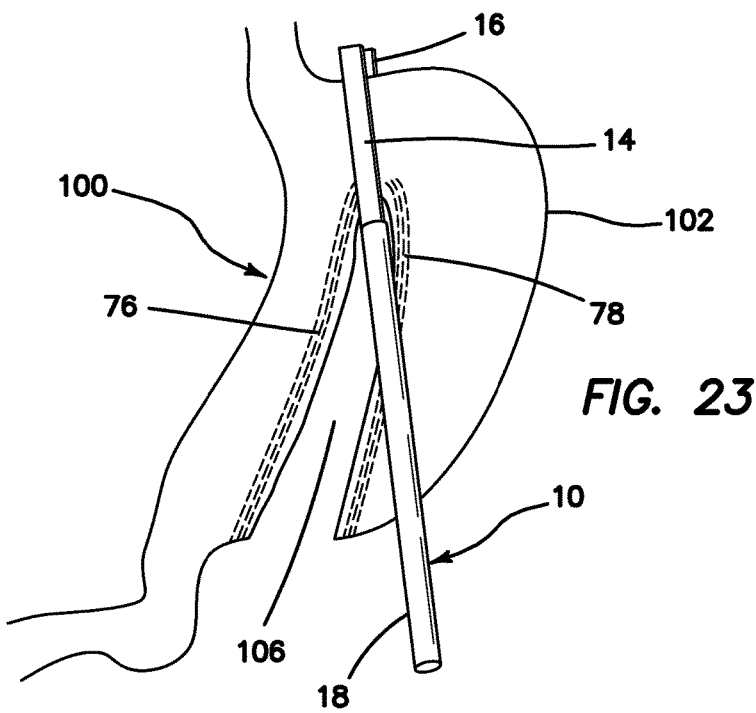
FIG. 23 is a perspective view of a surgical training instrument placed on a simulated tissue structure forward of a previous cut according to the present invention.
Figure 24:
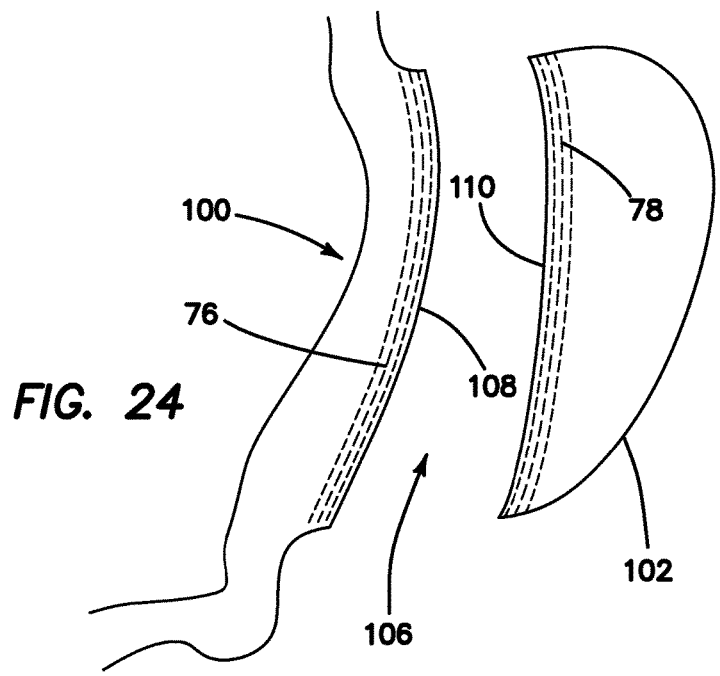
FIG. 24 is a perspective view of a dissected simulated tissue structure with markings according to the present invention.

With reference to FIGS. 18-24, there is shown a simulated organ 100 resembling a stomach configured for the purposes of practicing a surgical procedure such as a simulated gastric bypass procedure. In the simulated gastric bypass procedure, a portion 102 of a stomach 100 is amputated and removed from a body cavity. Although a stomach 100 is indicated, the stomach 100 is representative of other organs upon which similar resection procedures can be practiced. The procedure is commonly accomplished using a linear stapler along a prescribed path 104. In the case of simulation according to the present invention, a synthetic, elastomeric and/or fabric stomach 100 is provided with an occlusive and adherent internal surface such as from an adhesive or adhesive-like material. A simulated linear stapler 10 is configured to compress and cut the synthetic stomach 100 along a predetermined path 104. FIG. 19 shows a simulated linear stapler positioned on a simulated stomach 100. When activated, the upper and lower jaws 14, 16 of the simulated stapler 10 close to compress the material and a centrally moving blade cuts through the compressed material leaving a cut 106 and rows of markings 76, 78 of simulated staple deployment as shown in FIG. 20. The stapler 10 is then removed from the site and a simulated reloading of staple cartridges is performed, for example, by the removal and replacement of one or more marking elements 46, 54 if they are employed or by re-inking of ink-absorbent material on at least one of the opposing surfaces 15, 17, 34, 36, 50, 52 by compressing the jaws onto an ink pad. The stapler 10 is again introduced into the simulator or laparoscopic trainer 82 and placed upon the stomach 100 ahead of the cut 106 previously made as shown in FIG. 21. The action is repeated as shown in FIGS. 22-23 until the stomach 100 is completely divided as shown in FIG. 24 leaving two sealed sides 108, 110 with markings 76, 78 along the length of the amputated stomach 100. The hollow organ 100 comprises two adjacent simulated tissue surfaces that are brought into contact with each other and in the presence of adhesive or adherent material, the adjacent surfaces are glued. If no adhesive or adherent material is present, the compressed adjacent surfaces will not be adhered. Adhesive is selectively placed along one or more of the two adjacent surfaces, placing adhesive where the cut is desired and not locating adhesive where the surgical pathway is unwanted or surgically incorrect. Whereas, closing of the jaws on the hollow organ 100 brings the two adjacent surfaces into juxtaposition, contact, compression and adhesion in the location of adhesive, the two adjacent surfaces may be pre-adhered along a predetermined pathway that is most desirable for a practitioner to follow in order to achieve a desired clinical outcome in the simulation. Adjacent inner surfaces that are pre-adhered are glued together prior to application of the simulated training instrument 10, in particular, prior to the closure of the jaws onto the simulated tissue structure in the location of the two adjacent surfaces. In such a case, the surgical training instrument 10 does not play a role in adhering the two adjacent surfaces and only severs the pre-adhered surfaces. The simulated tissue structure is formed with a pre-adhered portion located along a predetermined pathway. The pre-adhered adjacent surfaces define the predetermined pathway 104 for the practitioner to follow. The presence of a predetermined pathway that is surgically or clinically significant for the particular procedure is a useful training tool indicating to the practitioner where the cut or stapling should be performed. In one variation, the predetermined pathway of pre-adhered adjacent surfaces is visible to the user. In another variation, the predetermined pathway of pre-adhered adjacent surfaces is only slightly visible to the user. In yet another variation, the predetermined pathway of pre-adhered adjacent surfaces is not visible to the user. These variations in the visibility of the predetermined pathway permit the selection of a simulated tissue structure having a level of difficulty that is appropriate for the experience level of the user. For example, a simulated tissue structure in which the predetermined pathway is visible to the user may be selected for the beginner and the tissue model with an invisible or slightly visible predetermined pathway may be chosen for the experienced practitioner. In one variation, the predetermined pathway is molded directly into the simulated tissue structure. The predetermined pathway includes a length and a width. The width of the predetermined pathway is at least as wide as the jaws such that when the jaws are placed on the predetermined pathway and the jaws are closed and the blade is activated to create a cut line in the simulated tissue, the simulated tissue structure advantageously remains sealed on either side of the cut line. Where the simulated tissue structure comprises a lumen, the predetermined pathway divides the lumen into two sections. If the simulated tissue structure is configured as a stomach, the predetermined pathway divides the stomach into two cavities.

It will be understood that many modifications can be made to the various disclosed embodiments without departing from the spirit and scope of the concept. For example, various sizes of the surgical devices are contemplated as well as various types of constructions and materials. It will also be apparent that many modifications can be made to the configuration of parts as well as their interaction. For these reasons, the above description should not be construed as limiting the invention, but should be interpreted as merely exemplary of preferred embodiments. Those skilled in the art will envision other modifications within the scope and spirit of the present invention.

I claim:

1. A surgical training system, comprising:
a simulated tissue structure comprising an outer surface, a first inner surface and a second inner surface adjacent to and at least partially facing the first inner surface;
a surgical training instrument having a first jaw and a second jaw connected to an elongate shaft such that at least one of the first jaw and second jaw is movable between an open position and a closed position with respect to the other one of the first jaw and second jaw; the first jaw has a first opposing surface and the second jaw has a second opposing surface; the elongate shaft is connected to a handle at a proximal end of the surgical training instrument; the handle is configured to manipulate at least one of the first jaw and the second jaw between the open position and the closed position; the surgical training instrument includes a blade configured to sever at least a portion of the simulated tissue structure placed between the first jaw and the second jaw to define a cut line in the simulated tissue structure;
wherein at least one of the first jaw and the second jaw includes a marking element configured to imprint markings on a portion of the outer surface of the simulated tissue structure placed between the first jaw and the second jaw when moved from the open position into contact with the simulated tissue structure in the closed position;
wherein the marking element is a sleeve-like structure having a lumen configured to receive the first jaw or the second jaw;
wherein the markings resemble at least one row of surgical staples on either side of the cut line.

2. The system of claim 1 wherein the marking element comprises a surface configured to carry a marking compound and release the marking compound in a pattern upon contact with the outer surface of the simulated tissue structure.

3. The system of claim 1 wherein the marking element contains ink, dye, or other marking compound.

4. The system of claim 1 further including a container comprising a first portion containing an inking element, a second portion configured to receive the distal end of the surgical training instrument in a preferred orientation that facilitates presentation of surfaces to be treated to the inking element and a third portion configured to seal the container.

5. The system of claim 1 wherein at least one of the first inner surface and second inner surface of the simulated tissue structure includes an adhesive configured to adhere the first inner surface to the second inner surface upon compression of the simulated tissue structure between the first jaw and the second jaw.

6. The system of claim 5 wherein the adhesive is a pressure-sensitive, adhesive, double-sided tape, or contact adhesive.

7. The system of claim 1 wherein the markings comprise ink, dye or other marking compound transferred from the marking element to the outer surface of the simulated tissue structure.

8. The system of claim 1 wherein the markings comprise a three-dimensional texturing or embossment.

9. The system of claim 1 further including adhesive on at least one of the first inner surface and the second inner surface.

* * * * *